(12) United States Patent
Fu et al.

(10) Patent No.: US 7,939,538 B2
(45) Date of Patent: *May 10, 2011

(54) COMPOUNDS, COMPOSITIONS AND METHODS FOR PREVENTION AND TREATMENT OF INFLAMMATORY AND IMMUNOREGULATORY DISORDERS AND DISEASES

(75) Inventors: Zice Fu, Foster City, CA (US); Michael G. Johnson, San Francisco, CA (US); An-Rong Li, South San Francisco, CA (US); Andrew P. Marcus, Berkeley, CA (US); Julio C. Medina, San Carlos, CA (US); Philippe Bergeron, San Mateo, CA (US); Xiaoqi Chen, Palo Alto, CA (US); Xiaohui Du, Foster City, CA (US); Jeffrey Deignan, San Francisco, CA (US); Jason A. Duquette, Millbrae, CA (US); Darin Gustin, Half Moon Bay, CA (US); Jeffrey T. Mihalic, San Francisco, CA (US); Jiwen Liu, Foster City, CA (US)

(73) Assignee: Amgen Inc., Thousand Oaks, CA (US)

( * ) Notice: Subject to any disclaimer, the term of this patent is extended or adjusted under 35 U.S.C. 154(b) by 1470 days.

This patent is subject to a terminal disclaimer.

(21) Appl. No.: 11/168,005

(22) Filed: Jun. 27, 2005

(65) Prior Publication Data
US 2006/0069099 A1 Mar. 30, 2006

Related U.S. Application Data

(60) Provisional application No. 60/583,901, filed on Jun. 28, 2004.

(51) Int. Cl.
*A61K 31/519* (2006.01)
*C07D 471/04* (2006.01)
*C07D 239/90* (2006.01)
*C07D 239/91* (2006.01)

(52) U.S. Cl. .................................... 514/264.1; 544/279
(58) Field of Classification Search ............... 514/264.1; 544/279
See application file for complete search history.

(56) References Cited

U.S. PATENT DOCUMENTS

| | | | |
|---|---|---|---|
| 5,202,322 A | 4/1993 | Allen et al. | |
| 5,256,667 A | 10/1993 | Allen et al. | |
| 5,719,144 A | 2/1998 | Hartman et al. | |
| 5,756,502 A | 5/1998 | Padia | |
| 5,869,665 A | 2/1999 | Padia | |
| 5,908,930 A | 6/1999 | Dow | |
| 6,140,064 A | 10/2000 | Loetscher et al. | |
| 6,545,005 B1 | 4/2003 | Baxter et al. | |
| 6,605,632 B1 | 8/2003 | Lesieur et al. | |
| 6,794,379 B2 * | 9/2004 | Medina et al. | 514/183 |
| 6,964,967 B2 * | 11/2005 | Huang et al. | 514/264.1 |
| 7,038,048 B2 * | 5/2006 | Lu et al. | 544/279 |
| 7,067,662 B2 * | 6/2006 | Medina et al. | 544/282 |
| 7,271,271 B2 | 9/2007 | Fu et al. | |
| 7,375,102 B2 * | 5/2008 | Fu et al. | 514/226.8 |
| 2002/0169159 A1 | 11/2002 | Medina et al. | |
| 2003/0055054 A1 | 3/2003 | Medina et al. | |
| 2003/0119854 A1 | 6/2003 | Schall et al. | |
| 2004/0077662 A1 | 4/2004 | Zhou et al. | |
| 2005/0075333 A1 | 4/2005 | Medina et al. | |
| 2006/0036093 A1 | 2/2006 | Lin et al. | |
| 2007/0015773 A1 | 1/2007 | Bergeron et al. | |

FOREIGN PATENT DOCUMENTS

| | | |
|---|---|---|
| EP | 0481 614 A1 | 4/1992 |
| WO | WO99/58495 | 11/1995 |
| WO | WO98/26664 | 6/1998 |
| WO | WO01/16114 A2 | 3/2001 |
| WO | WO01/16114 A3 | 3/2001 |
| WO | WO01/19800 A2 | 3/2001 |
| WO | WO01/19800 A3 | 3/2001 |
| WO | WO01/30768 | 5/2001 |
| WO | WO01/62758 | 8/2001 |
| WO | WO01/98278 | 12/2001 |
| WO | WO02/083413 | 10/2002 |
| WO | WO03/076418 | 9/2003 |
| WO | WO2004/075863 | 9/2004 |
| WO | PCT/US2005/023251 | 11/2005 |

OTHER PUBLICATIONS

Balashov et al., 1999 "CCR5+ and CXCR3+ T Cells are Increased in Multiple Sclerosis and Their Ligands MIP-1α and IP-10 are Expressed in Demyelinating Brain Lesions," Proc. Natl. Acad. Sci. USA, 96:6873-78.

(Continued)

*Primary Examiner* — James O Wilson
*Assistant Examiner* — Tamthom N Truong
(74) *Attorney, Agent, or Firm* — G. Prabhakar Reddy

(57) ABSTRACT

Compounds are provided having the formula:

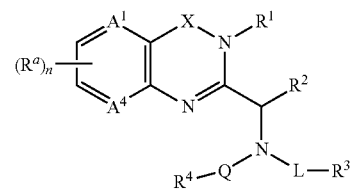

wherein variables $R^a$, $R^1$, $R^2$, $R^3$, $R^4$, $A^1$, $A^4$, L, Q, X and subscript n as described herein. The subject compounds are useful for treatment of inflammatory and immune conditions and diseases. Compositions and methods of treatment using the subject compounds are also provided. For example, the subject methods are useful for treatment of inflammatory and immune disorders and disease such as multiple sclerosis, rheumatoid arthritis, psoriasis, and inflammatory bowel disease.

23 Claims, 3 Drawing Sheets

OTHER PUBLICATIONS

U.S. Appl. No. 11/168,006, filed Jun. 27, 2005, Fu et al.
U.S. Appl. No. 11/168,193, filed Jun. 27, 2005, Fu et al.
Bowdish et al. 2003 "Evaluation of an Oral CXCR3 Antagonist in a Rat Model of the Acute Allograft Rejection", *The Journal of the Heart and Lung Association* vol. 22 Supplement 1 p. S162.
Carter, et al., 2002 "Chemokine Receptor Antagonism as an Approach to Anti-Inflammatory Therapy: 'Just Right' or Plain Wrong?", *Current Opin. Chem. Biol.*, 6: 510-525.
Fife et al., 2001 "CXCL10 (IFN-γ-Inducible Protein-10) Control of Encephalitogenic CD4$^+$T Cell Accumulation in the Central Nervous System During Experimental Autoimmune Encephalomyelitis", *J. Immunol.* 166: 7617-7624.
Gerard et al., 2001 "Chemokines and Diseases", *Nature Immunology*, 2(2): 108-115.
Goldberg et al., 2001 "CXCR3 Expression in Human Central Nervous System Diseases", Neuropathol. Appl. Neurobiol. 27(2):127-38.
Hancock et al., 2000 "Requirement of the Chemokine Receptor CXCR3 for Acute Allograft Rejection," *J. Exp. Med.*, 192(10):1515-19.
Hancock et al., 2001 "Donor-Derived IP-10 Initiates Development of Acute Allograft Rejection", *J. Exp. Med.* 193: 975-980.
Liu et al., 2001 "Neutralization of the Chemokine CXCL10 Reduces Inflammatory Cell Invasion and Demyelination and Improves Neurological Function in a Viral Model of Multiple Sclerosis", *J. Immunol.* 167: 4091-4097.
Melter et al., 2001"Expression of the Chemokine Receptor CXCR3 and Its Ligand IP-10 During Cardiac Allograft Rejection", *Circulation* 104: 2558-2564.
Onuffer, et al., 2002 "Chemokines, Chemokine Receptors and Small-Molecule Antagonists: Recent Developments", Trends in Pharmacological Sciences 23(10): 459-467.
Padia, J.K., et al., "Design and synthesis of novel nonpeptide CCK-B receptor antagonists," Bioorganic & Medicinal Chemistry Letters, Oxford, GB, vol. 7, No. 7, Apr. 8, 1997, pp. 805-810.
Proudfoot, et al., 2003 "Strategies for Chemokine Antagonists as Therapeutics", *Seminars in Immunology.* 15:57-65.
Qin et al., 1998 "The Chemokine Receptors CXCR3 and CCR5 Mark Subsets of T Cells Associated with Certain Inflammatory Reactions," *J. Clin. Invest.* 101(4): 746-54.
Rabin et al., 1999 "Chemokine Receptor Responses on T Cells Achieved Through Regulation of Both Receptor Expression and Signaling," *The Journal of Immunology*, 162: 3840-50.
Rottman et al., 2001 "Potential Role of the Chemokine Receptors CXCR3, CCR4, and the Integrin αEβ7 in the Pathogenesis of Psoriasis Vulgaris", *Lab. Invest.* 81(3): 335-347.
Ruschpler et al., 2003 "Hign CXCR3 Expression in nSynovial Mast Cells Associated with CXCL9 and CXCL10 Expression in Inflammatory Synovial Tissues of Patients with Rheumatoid Arthritis", *Arthritis Res. Ther.* 5: R241-R252.
Sasaki et al., Nov. 2002 "Blockade of CXCL10 Protects Mice From Acute Colitis and Enhances Crypt Cell Survival", *Eur. J. Immunol.* 32: 3197-31205.
Sorensen et al., 1999 "Expression of Specific Chemokines and Chemokine Receptors in the Central Nervous System of Multiple Sclerosis Patients", *J. Clinical Invest.* 103: 807-815.
Wells, et al., 1999 "Chemokine Receptors and Their Antagonists in Allergic Lung Disease" *Inflamm. Res.*, 48: 353-362.

\* cited by examiner a. NMM, CH₂Cl₂, -20° C, 12h; b. CH₂Cl₂, -20° C, 4h; c. NMM, CH₂Cl₂, -20° C, 2h; d. cat. Pd-on-carbon, 1,3-cyclohexadiene, EtOH, RT.

a. KI, $K_2CO_3$, DMF, RT-80° C; b. NMM, EDC, HOBT, DMF, RT; c. TFA, $CH_2Cl_2$, 0° C-RT; d. KI, $K_2CO_3$, DMF, RT-80° C; e. $Na(OAc)_3BH$, DCE, 0° C-RT.

a. Na(OAc)$_3$BH, DCE, 0° C-RT; b. NMM, EDC, HOBT, DMF, RT; c. TFA, CH$_2$Cl$_2$, 0° C-RT.

COMPOUNDS, COMPOSITIONS AND METHODS FOR PREVENTION AND TREATMENT OF INFLAMMATORY AND IMMUNOREGULATORY DISORDERS AND DISEASES

1. CROSS-REFERENCE TO RELATED APPLICATION

This application claims the benefit of U.S. provisional application No. 60/583,901, filed Jun. 28, 2004, the disclosure of which is incorporated herein by reference in its entirety.

2. FIELD OF THE INVENTION

The present invention relates to novel modulators of the CXCR3 receptor, compositions comprising the novel compounds and methods of their use for the treatment of, for example, inflammatory and immunoregulatory disorders and diseases, including asthma and allergic diseases, as well as autoimmune pathologies such as rheumatoid arthritis, multiple sclerosis, inflammatory bowel disease, psoriasis and atherosclerosis.

3. BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3:165-183 (1991), Schall, et al., *Curr. Opin. Immunol.*, 6:865-873 (1994) and Murphy, *Rev. Immun.*, 12:593-633 (1994)). In addition to stimulating chemotaxis, other changes can be selectively induced by chemokines in responsive cells, including changes in cell shape, transient rises in the concentration of intracellular free calcium ions ($[Ca^{2+}]_i$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

There are four classes of chemokines, CXC ($\alpha$), CC($\beta$), C($\gamma$), and $CX_3C$ ($\delta$), depending on whether the first two cysteines are separated by a single amino acid (C-X-C)), are adjacent (C-C), have a missing cysteine pair (C), or are separated by three amino acids ($CX_3C$). The $\alpha$-chemokines, such as interleukin-8 (IL-8), melanoma growth stimulatory activity protein (MGSA), and stromal cell derived factor 1 (SDF-1) are chemotactic primarily for neutrophils and lymphocytes, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., *Nature*, 381: 661-666 (1996)). The C chemokine lymphotactin shows specificity for lymphocytes (Kelner, et al., *Science*, 266: 1395-1399 (1994)) while the $CX_3C$ chemokine fractalkine shows specificity for lymphocytes and monocytes (Bazan, et al., *Nature*, 385:640-644 (1997)).

Chemokines bind specific cell-surface receptors belonging to the family of G-protein-coupled seven-transmembrane-domain proteins (reviewed in Horuk, *Trends Pharm. Sci.*, 15:159-165 (1994)) termed "chemokine receptors." On binding their cognate ligands, chemokine receptors transduce an intracellular signal through the associated heterotrimeric G protein, resulting in a rapid increase in intracellular calcium concentration. There are at least twelve human chemokine receptors that bind or respond to $\beta$-chemokines with the following characteristic pattern: CCR1 (or "CKR-1" or "CC-CKR-1") MIP-1$\alpha$, MIP-1$\beta$, MCP-3, RANTES (Ben-Baruch, et al., *J. Biol. Chem.*, 270:22123-22128 (1995); Neote, et al., *Cell*, 72:415-425 (1993)); CCR2A and CCR2B (or "CKR-2A"/"CKR-2A" or "CC-CKR-2A"/"CC-CKR2A") MCP-1, MCP-3, MCP-4; CCR3 (or "CKR-3" or "CC-CKR-3") eotaxin, RANTES, MCP; (Ponath, et al., *J. Exp. Med.*, 183:2437-2448 (1996)); CCR4 (or "CKR-4" or "CC-CKR-4") TARC, MDC (Imai, et al., *J. Biol. Chem.*, 273:1764-1768 (1998)); CCR5 (or "CKR-5" or "CC-CKR-5") MIP-1$\alpha$, RANTES, MIP-1$\beta$ (Sanson, et al., *Biochemistry*, 35:3362-3367 (1996)); CCR6 MIP-3 alpha (Greaves, et al., *J. Exp. Med.*, 186:837-844 (1997)); CCR7 MIP-3 beta and 6Ckine (Campbell, et al., *J. Cell. Biol.*, 141:1053-1059(1998)); CCR8 I-309, HHV8 vMIP-I, HHV-8 vMIP-II, MCV vMCC-I (Dairaghi, et al., *J. Biol. Chem.*, 274:21569-21574 (1999)); CCR9 TECK (Zaballos, et al., *J. Immunol.*, 162:5671-5675 (1999)), D6 MIP-1 beta, RANTES, and MCP-3 (Nibbs, et al., *J. Biol. Chem.*, 272:32078-32083 (1997)), and the Duffy blood-group antigen RANTES, MCP-1 (Chaudhun, et al., *J. Biol. Chem.*, 269:7835-7838 (1994)).

Chemokine receptors, such as CCR1, CCR2, CCR2A, CCR2B, CCR3, CCR4, CCR5, CCR6, CCR7, CCR8, CCR9, CXCR1, CXCR2, CXCR3, CXCR4, CXCR5, $CX_3CR1$, and XCR1 have been implicated as being important mediators of inflammatory and immunoregulatory disorders and diseases, including asthma and allergic diseases, as well as autoimmune pathologies such as rheumatoid arthritis and atherosclerosis.

The CXCR3 chemokine receptor is expressed primarily in T lymphocytes, and its functional activity can be measured by cytosolic calcium elevation or chemotaxis. The receptor was previously referred to as GPR9 or CKR-L2. Its chromosomal location is unusual among the chemokine receptors in being localized to Xq13. Ligands that have been identified that are selective and of high affinity are the CXC chemokines, IP10, MIG and ITAC.

The highly selective expression of CXCR3 makes it an ideal target for intervention to interrupt inappropriate T cell trafficking. The clinical indications for such intervention are in T-cell mediated autoimmune diseases such as multiple sclerosis, rheumatoid arthritis, and type I diabetes, for example. Inappropriate T-cell infiltration also occurs in psoriasis and other pathogenic skin inflammation conditions, although the diseases may not be true autoimmune disorders. In this regard, up-regulation of IP-10 expression in keratinocytes is a common feature in cutaneous immunopathologies. Inhibition of CXCR3 can be beneficial in reducing rejection in organ transplantation. Ectopic expression of CXCR3 in certain tumors, especially subsets of B cell malignancies, indicates that selective inhibitors of CXCR3 will have value in tumor immunotherapy, particularly attenuation of metastasis.

In view of the clinical importance of CXCR3, compounds that modulate CXCR3 function can be used for the development of new therapeutic agents. Such compounds are provided herein.

4. SUMMARY OF THE INVENTION

The present invention provides compounds that are useful in the treatment or prevention of certain inflammatory and immunoregulatory disorders and diseases, including asthma, psoriasis, inflammatory bowel disease and allergic diseases, as well as autoimmune pathologies such as rheumatoid arthritis and multiple sclerosis. In one aspect, the compounds provided have the general formula (I):

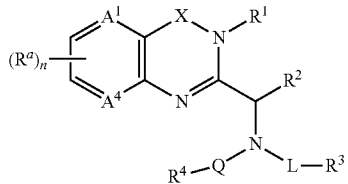

wherein $A^1$ and $A^4$ independently are C(Rb) or N; Q is a member selected from the group consisting of a bond, $(C_1-C_8)$alkylene, $(C_2-C_8)$heteroalkylene, —C(O)—, —OC(O)—, —CH$_2$CO—, —CH$_2$SO— and —CH$_2$SO$_2$—; L is a bond or $(C_1-C_5)$alkyl; X is —CH$_2$—, SO$_2$ or —C(O)—; $R^a$ is selected from the group consisting of —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$; $R^b$ is selected from the group consisting of —OR', =O, =NR', =N—OR', —NR'R", —SR', -halogen, —SiR'R" R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —R', —S(O)R', —S(O)$_2$R', —S(O)$_2$NR'R", —CN and —NO$_2$; the subscript n is 0, 1, 2 or 3; each R', R" and R''' independently is H, unsubstituted $(C_1-C_8)$alkyl, heteroalkyl, unsubstituted aryl, or substituted aryl; $R^1$ is heteroaryl or aryl; $R^2$ is a member selected from the group consisting of hydrogen, halogen, $(C_1-C_{10})$alkyl, $(C_2-C_{10})$heteroalkyl, hetero$(C_1-C_{10})$cycloalkyl, $(C_1-C_{10})$alkylaryl, and $(C_2-C_{10})$heteroalkylaryl or optionally R may be combined with L to form a 5-, 6-, 7- or 8-membered ring containing from 1 to 3 heteroatoms selected from the group consisting of N, O and S; $R^3$ is absent or is a member selected from the group consisting of —H, —CHR$^6$R$^7$, —S(O)$_m$R$^5$, —S(O)$_m$N(R$^8$)R$^9$, —S(O)$_m$N(R$^8$)CH$_2$R$^6$, —N(R$^8$)SO$_2$R$^5$, —N(R$^8$)CH$_2$R$^{10}$,

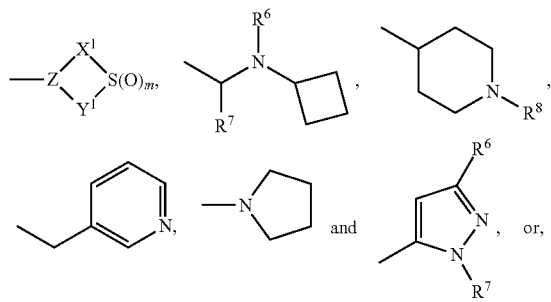

optionally, $R^3$ may be combined with $R^2$ to form a 4-, 5-, 6-, 7- or 8-membered ring containing from 1 to 3 heteroatoms selected from the group consisting of N, O and S; $R^4$ is a member selected from the group consisting of $(C_1-C_{20})$alkyl, $(C_2-C_{20})$heteroalkyl, heteroaryl, aryl, heteroaryl$(C_1-C_6)$alkyl, heteroaryl$(C_2-C_6)$heteroalkyl, aryl$(C_1-C_6)$alkyl and aryl$(C_2-C_6)$heteroalkyl; $R^5$ is selected from the group consisting of $(C_1-C_8)$alkyl, $(C_2-C_8)$heteroalkyl, aryl and heteroaryl; $R^6$ and $R^7$ independently are hydrogen, $(C_1-C_8)$alkyl or $(C_2-C_8)$heteroalkyl, $R^8$ is hydrogen, $(C_1-C_8)$alkyl, $(C_2-C_8)$heteroalkyl, heteroaryl or aryl, $R^9$ is $(C_1-C_8)$alkyl; $R^{10}$ is aryl; Z is CH or N; $X^1$ is a bond, $(C_1-C_6)$alkylene or $(C_1-C_6)$heteroalkylene; $Y^1$ is $(C_1-C_6)$alkylene; and the subscript m is 0, 1 or 2.

In another aspect, the compounds provided have the formula (III):

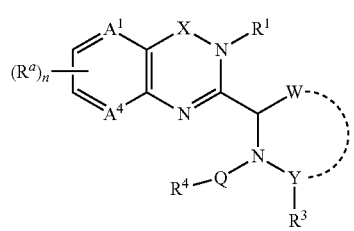

wherein $A^1$ and $A^4$ independently are $C(R^b)$ or N; Q is a member selected from the group consisting of a bond, $(C_1-C_8)$alkylene, $(C_2-C_8)$heteroalkylene, —C(O)—, —OC(O)—, —CH$_2$CO—, —CH$_2$SO— and —CH$_2$SO$_2$—; each of W and Y is independently a carbon or a heteroatom and W and Y are linked together to form a 5- or 6-membered cycloalkyl or cycloheteroalkyl ring, wherein the 5- or 6-membered ring is unsubstituted or substituted with halogen, NH$_2$, NO$_2$, $(C_1-C_{20})$alkyl, $(C_2-C_{20})$heteroalkyl, heteroaryl, aryl, heteroaryl$(C_1-C_6)$alkyl, heteroaryl$(C_2-C_6)$heteroalkyl, aryl$(C_1-C_6)$alkyl and aryl$(C_2-C_6)$heteroalkyl; X is —CH$_2$—, SO$_2$ or —C(O)—; Ra is selected from the group consisting of —OR', =O, =NR', =N—OR', —NR'R", —SR', -halogen, —SiR'R"R''', —OC(O)R', —C(O)R, —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R"—CN and —NO$_2$; $R^b$ is selected from the group consisting of —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR, —S(O)R', —S(O)$_2$R', —S(O)$_2$NR'R", —CN and —NO$_2$; the subscript n is 0, 1, 2 or 3; each R', R" and R''' independently is H, unsubstituted $(C_1-C_8)$alkyl, heteroalkyl, unsubstituted aryl, or substituted aryl; $R^1$ is heteroaryl or aryl; $R^3$ is absent or is a member selected from the group consisting of —H, —CHR$^6$R$^7$, —S(O)$_m$R$^5$, —S(O)$_m$N(R$^8$)R$^9$, —S(O)$_m$ N(R$^8$)CH$_2$R$^6$, —N(R$^8$)SO$_2$R$^5$, —N(R$^8$)CH$_2$R,

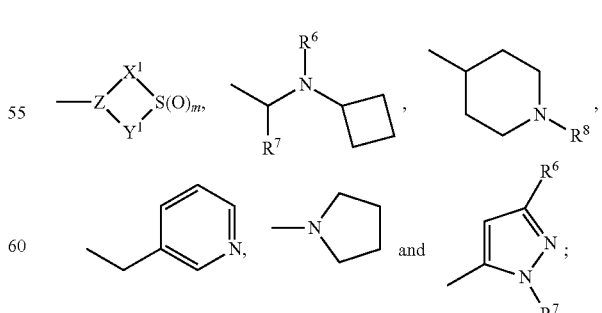

$R^4$ is a member selected from the group consisting of $(C_1-C_{20})$alkyl, $(C_2-C_{20})$heteroalkyl, heteroaryl, aryl, heteroaryl$(C_1-C_6)$alkyl, heteroaryl$(C_2-C_6)$heteroalkyl, aryl$(C_1-C_6)$ alkyl and aryl($C_2$-$C_6$)heteroalkyl; $R^5$ is selected from the group consisting of ($C_1$-$C_8$)alkyl, ($C_2$-$C_8$)heteroalkyl, aryl and heteroaryl; $R^6$ and $R^7$ independently are hydrogen, ($C_1$-$C_8$)alkyl or ($C_2$-$C_8$)heteroalkyl; $R^8$ is hydrogen, ($C_1$-$C_8$) alkyl, ($C_2$-$C_8$)heteroalkyl, heteroaryl or aryl, $R^9$ is ($C_1$-$C_8$) alkyl; and $R^{10}$ is aryl.

The compounds of the invention include pharmaceutically acceptable salts, solvates or prodrugs thereof.

In another aspect, the present invention provides pharmaceutical compositions comprising a compound of formula (I) or (III) and a pharmaceutically acceptable excipient or carrier.

In a further aspect, the present invention provides methods for the treatment or prevention of an inflammatory or immune condition or disorder, comprising administering to a subject in need of such treatment or prevention a therapeutically effective amount of a compound of formula (I) or (III). Preferred subjects for the methods of the invention include mammals such as humans.

The present invention also provides methods for the treatment or prevention of a condition or disorder mediated by the CXCR3 chemokine receptor, comprising administering to a subject in need of such treatment or prevention a therapeutically effective amount of a compound of formula (I) or (III).

The present invention also provides methods for the modulation of CXCR3, comprising contacting a cell with a compound of formula (I) or (III).

The present invention further provides methods for the modulation of CXCR3, comprising contacting a CXCR3 protein with a compound of formula (I) or (III).

In addition, the present invention provides methods of making compounds of formula (I) or (III).

5. BRIEF DESCRIPTION OF THE DRAWINGS

6. DETAILED DESCRIPTION OF THE INVENTION

6.1 Definitions

Figure 1:
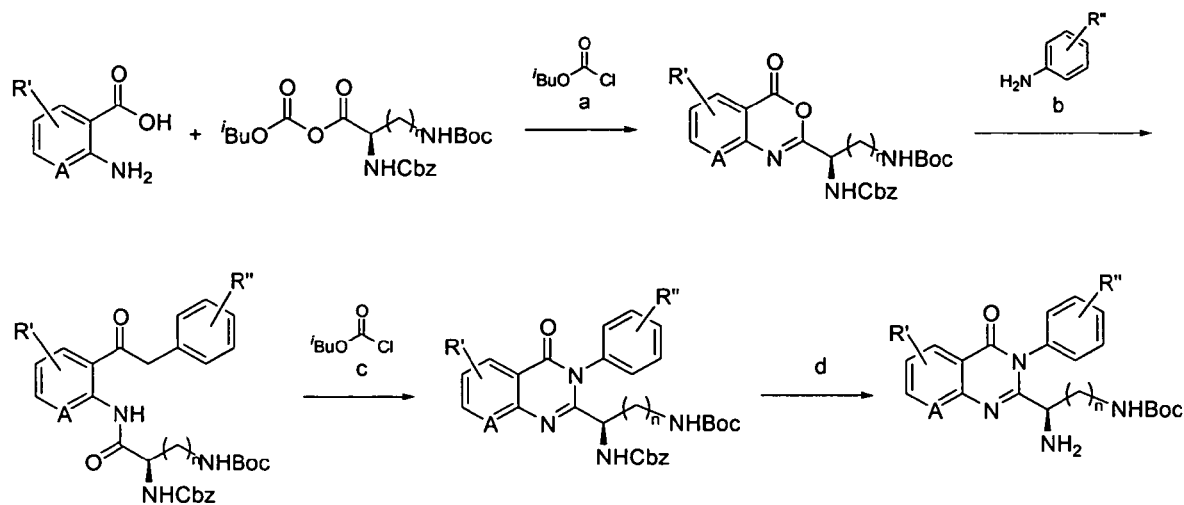
FIG. 1 illustrates a general synthesis scheme for preparation of compounds of the invention.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups that can be the same or different.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2H_2$—NH—$CH_3$, —$CH_2$—$CH_2$—N($CH_3$—)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)$CH_3$. Up to two heteroatoms may be consecutive, such as, for example, —$CH_2$—NH—$OCH_3$ and —$CH_2$—O—Si ($CH_3$)$_3$. When a prefix such as ($C_2$-$C_8$) is used to refer to a heteroalkyl group, the number of carbons (2-8, in this example) is meant to include the heteroatoms as well. For example, a $C_2$-heteroalkyl group is meant to include, for example, —$CH_2$OH (one carbon atom and one heteroatom replacing a carbon atom) and —$CH_2$SH. The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'C(O)NR"R"', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2 m+1), where m is the total number of carbon atoms in such radical. R', R" and R"' each independently refer to H, unsubstituted (C$_1$-C$_8$) alkyl and heteroalkyl, unsubstituted aryl, aryl substituted with 1-3 halogens, alkoxy or thioalkoxy groups, or aryl-(C$_1$-C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" in its broadest sense is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Preferably, the alkyl groups will have from 0-3 substituents, more preferably 0, 1, or 2 substituents, unless otherwise specified.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R, —NR'—C(O)NR"R"', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro (C$_1$-C$_4$)alkoxy, and perfluoro(C$_1$-C$_4$)alkyl, in a number ranging from zero to the total number of open valences on the aromatic ring system; and where R', R" and R"' are independently selected from H, (C$_1$-C$_8$)alkyl and heteroalkyl, unsubstituted aryl and heteroaryl, (unsubstituted aryl)-(C$_1$-C$_4$) alkyl, and (unsubstituted aryl)oxy-(C$_1$-C$_4$)alkyl.

Two of the substituents on adjacent atoms of the aryl or heteroaryl ring may optionally be replaced with a substituent of the formula -T-C(OHCH$_2$)$_q$—U—, wherein T and U are independently —NH—, —O—, —CH$_2$ or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is O, —NR'—, —S—, —S(O), —S(O)$_2$—, or —S(O)$_2$NR'—. The substituent R' in —NR'— and —S(O)$_2$NR'— is selected from hydrogen or unsubstituted (C$_1$-C$_6$)alkyl.

As used herein, the term "heteroatom" is meant to include oxygen (O), nitrogen (N), sulfur (S) and silicon (Si).

As used herein, the abbreviation "Me" is meant to be methyl (i.e., —CH$_3$), the abbreviation "Et" is meant to be ethyl, and the abbreviation "Ph" is meant to be phenyl.

The term "pharmaceutically acceptable salts" is meant to include salts of the compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, et al. (1977) *J. Pharm. Sci.* 66:1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the active compounds described herein are inactive compounds that readily undergo chemical changes under physiological conditions to provide active compounds of the present invention. Additionally, prodrugs can be converted to active compounds of the present invention by chemical or biochemical methods in an ex vivo environment. For example, prodrugs can be slowly converted to active compounds of the present invention when placed in a transdermal patch reservoir with a suitable enzyme or chemical reagent. Prodrugs are often useful because, in some situations, they may be easier to administer than the active compound. They may, for instance, be bioavailable by oral administration whereas the active compound is not. The prodrug may also have improved solubility in pharmacological compositions over the active compound. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of an active compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, enantiomers, diastereomers, geometric isomers and individual isomers are all intended to be encompassed within the scope of the present invention.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. It should be noted that if the stereochemistry of a structure or a portion of a structure is not indicated with, for example, bold or dashed lines, the structure or portion of the structure is to be interpreted as encompassing all stereoisomers of it.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N.Y., 1962); and Wilen, S. H., *Tables of Resolving Agents and Optical Resolutions* p. 268 (E. L. Eliel, Ed., Univ. of Notre Dame Press, Notre Dame, Ind., 1972).

The compounds of the present invention may also contain unnatural proportions of atomic isotopes at one or more of the atoms that constitute such compounds. For example, the compounds may be radiolabeled with radioactive isotopes, such as for example tritium (3H), iodine-125 ($^{125}$I) or carbon-14 ($^{14}$C). Radiolabeled compounds are useful as therapeutic agents, e.g., cancer therapeutic agents, research reagents, e.g., binding assay reagents, and diagnostic agents, e.g., in vivo imaging agents. All isotopic variations of the compounds of the present invention, whether radioactive or not, are intended to be encompassed within the scope of the present invention.

As used herein, the term "active" means effective to modulate, e.g., inhibit, CXCR3 function.

The terms "treat", "treating" or "treatment", as used herein, refer to a method of alleviating or abrogating a disease and/or its attendant symptoms. The terms "prevent", "preventing" or "prevention", as used herein, refer to a method of barring a subject from acquiring a disease.

6.2 Embodiments of the Invention

The present invention is directed to compounds, compositions and methods useful in the modulation of chemokine receptor activity, particularly CXCR3. The compounds of the invention are useful for the treatment of, for example, inflammatory and immunoregulatory disorders, and can be administered directly to subjects, for example, humans, as formulated pharmaceuticals. The compounds of the invention are also useful for identifying and/or designing compounds that modulate CXCR3 function, e.g., CXCR3 antagonists, and compounds that are converted to one or more compounds that modulate CXCR3 function under physiological conditions.

The compounds of the present invention are those which inhibit at least one function or characteristic of a mammalian CXCR3 protein, for example, a human CXCR3 protein. The ability of a compound to inhibit such a function can be demonstrated in a binding assay (e.g., ligand binding or agonist binding), a signaling assay (e.g., activation of a mammalian G protein, induction of rapid and transient increase in the concentration of cytosolic free calcium), and/or cellular response function (e.g., stimulation of chemotaxis, exocytosis or inflammatory mediator release by leukocytes). Exemplary assays are described in U.S. Patent Application Publication Nos. 2002/0169159 A1, and 2003/0055054 A1, the contents of which are each hereby incorporated by reference in their entirety.

6.3 Compounds

The present invention provides compounds that are useful as antagonists of CXCR3, having particular utility for the treatment or prevention of inflammatory or immune conditions or disorders.

In one aspect, the present invention provides a compound having the formula (I):

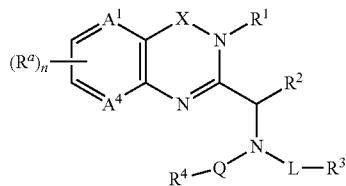

wherein $R^a$, $R^1$, $R^2$, $R^3$, $R^4$, $A^1$, $A^4$, L, Q, X and subscript n are as defined below. The compounds provided in the above formula include pharmaceutically acceptable salts, solvates or prodrugs thereof, unless otherwise indicated.

$A^1$ and $A^4$ independently are $C(R^b)$ or N.

In some embodiments, $A^4$ is N.

In some embodiments, $A^4$ is $C(R^b)$.

In some embodiments, $A^1$ is CH.

In some embodiments, $A^4$ is CH.

Q is a member selected from the group consisting of a bond, $(C_1-C_8)$alkylene, $(C_2-C_8)$heteroalkylene, —C(O)—, —OC(O)—, —$CH_2$CO—, —$CH_2$SO— and —$CH_2SO_2$—.

In some embodiments, Q is —C(O)—.

L is a bond or $(C_1-C_5)$alkylene.

In some embodiments, L is a bond, —$CH_2$— or —$CH_2CH_2$—.

X is —$CH_2$—, $SO_2$ or —C(O)—.

In certain embodiments, X is —C(O)—.

$R^a$ is selected from the group consisting of —OR', =O, =NR', =N—OR', —NR'R", —SR', -halogen, —SiR'R" R'", —OC(O)R', —C(O)R', —$CO_2$R', —CONR'R", —OC(O)NR'R", —NR"C(O)R', —NR'—C(O)NR"R'", —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —CN and —$NO_2$.

$R^b$ is selected from the group consisting of —OR', =O, =NR', =N—OR', —NR'R", —SR', -halogen, —SiR'R" R'", —OC(O)R', —C(O)R', —$CO_2$R', —CONR'R", —OC(O)NR'R", —NR"C(O)R', —NR'—C(O)NR"R'", —NR"C(O)$_2$R', —NH—C($NH_2$)=NH, —NR'C($NH_2$)=NH, —NH—C($NH_2$)=NR', —R', —S(O)R', —S(O)$_2$R', —S(O)$_2$NR'R", —CN and —$NO_2$.

The subscript n is 0, 1, 2 or 3.

Each R', R" and R'" independently is H, unsubstituted $(C_1-C_8)$alkyl, heteroalkyl, unsubstituted aryl, or substituted aryl.

$R^1$ is heteroaryl or aryl.

In certain embodiments, $R^1$ is a unsubstituted or a meta- or para-substituted phenyl, wherein the substituent is a halogen, cyano, $(C_1-C_8)$alkyl, $(C_1-C_8)$heteroalkyl, $(C_1-C_8)$alkoxy, or $(C_1-C_8)$heteroalkoxy.

In some embodiments, $R^1$ is para-cyanophenyl.

$R^2$ is a member selected from the group consisting of hydrogen, halogen, $(C_1-C_{10})$alkyl, $(C_2-C_{10})$heteroalkyl, hetero$(C_1-C_{10})$cycloalkyl, $(C_1-C_{10})$alkylaryl, and $(C_2-C_{10})$heteroalkylaryl or optionally $R^2$ may be combined with L to form a 5-, 6-, 7- or 8-membered ring containing from 1 to 3 heteroatoms selected from the group consisting of N, O and S.

In some embodiments, $R^2$ is a member selected from the group consisting of

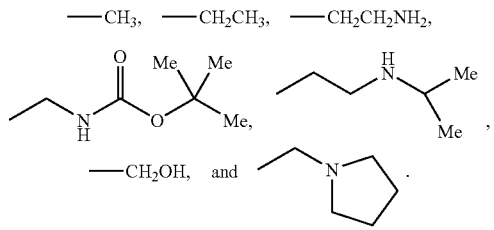

$R^3$ is absent or is a member selected from the group consisting of —H, —$CHR^6R^7$, —$S(O)_mR^5$, $S(O)_mN(R^8)R^9$, $S(O)_mN(R^8)CH_2R^6$, —$N(R^8)SO_2R^5$, —$N(R^8)CH_2R^{10}$,

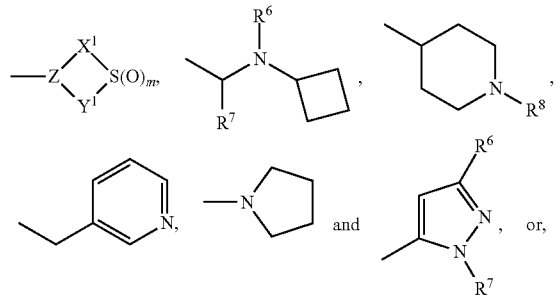

optionally, $R^3$ may be combined with $R^2$ to form a 4-, 5-, 6-, 7- or 8-membered ring containing from 1 to 3 heteroatoms selected from the group consisting of N, O and S.

In certain embodiments, $R^3$ is a member selected from the group consisting of

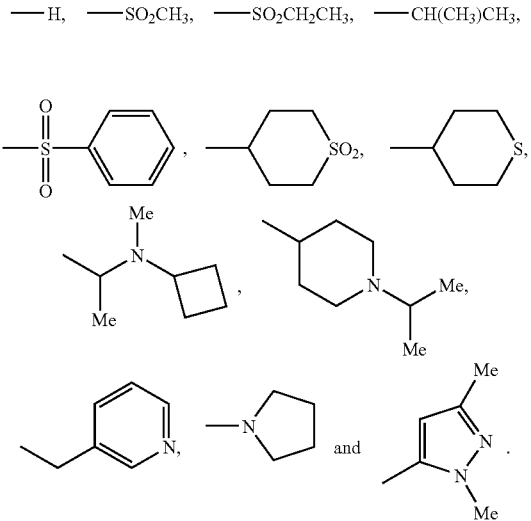

In certain embodiments, -L-$R^3$ when taken together is

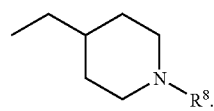

$R^4$ is a member selected from the group consisting of $(C_1\text{-}C_{20})$alkyl, $(C_2\text{-}C_{20})$heteroalkyl, heteroaryl, aryl, heteroaryl$(C_1\text{-}C_6)$alkyl, heteroaryl$(C_2\text{-}C_6)$heteroalkyl, aryl$(C_1\text{-}C_6)$alkyl and aryl$(C_2\text{-}C_6)$heteroalkyl.

In certain embodiments, $-Q-R^4$ is

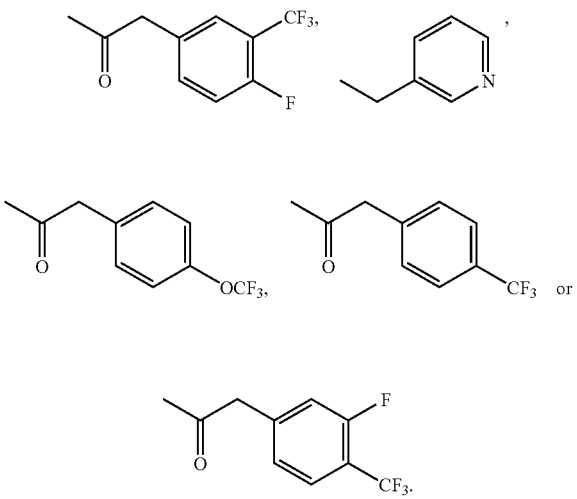

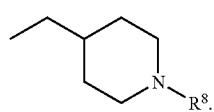

$R^5$ is selected from the group consisting of $(C_1\text{-}C_8)$alkyl, $(C_2\text{-}C_8)$heteroalkyl, aryl and heteroaryl.

$R^6$ and $R^7$ independently are hydrogen, $(C_1\text{-}C_8)$alkyl or $(C_2\text{-}C_8)$heteroalkyl.

$R^8$ is hydrogen, $(C_1\text{-}C_8)$alkyl, $(C_2\text{-}C_8)$heteroalkyl, heteroaryl or aryl.

$R^9$ is $(C_1\text{-}C_8)$alkyl.

$R^{10}$ is aryl.

Z is CH or N.

$X^1$ is a bond, $(C_1\text{-}C_6)$alkylene or $(C_1\text{-}C_6)$heteroalkylene.

$Y^1$ is $(C_1\text{-}C_6)$alkylene.

The subscript m is 0, 1 or 2.

In some embodiments, the compound has the formula (II):

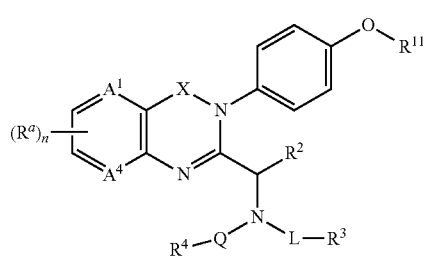

where $R^a$, $R^2$, $R^3$, $R^4$, $A^1$, $A^4$, L, Q, X and subscript n are as described above in formula I, $R^{11}$ is hydrogen, $(C_1\text{-}C_8)$alkyl or $(C_2\text{-}C_8)$heteroalkyl.

In certain embodiments, $R^{11}$ is —H, —CH$_3$, —CH$_2$CH$_3$, or —CH$_2$CF$_3$ In certain embodiments, $R^2$ is methyl and -L-$R^3$ is In certain embodiments, $R^3$ is a member selected from the group consisting of

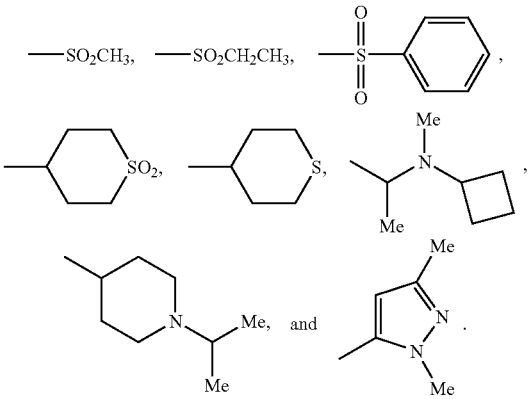

In certain embodiments, a compound of the present invention has the formula (III):

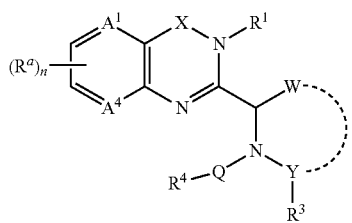

wherein $R^a$, $R^1$, $R^3$, $R^4$, $A^1$, $A^4$, Y, Q, X and subscript n are as defined below. The compounds provided in the above formula include pharmaceutically acceptable salts, solvates or prodrugs thereof, unless otherwise indicated.

$A^1$ and $A^4$ independently are $C(R^b)$ or N.

In some embodiments, $A^4$ is N.

In some embodiments, $A^1$ is $C(R^b)$.

In some embodiments, $A^4$ is $C(R^b)$.

In some embodiments, $A^4$ is —CH$_2$—.

Q is a member selected from the group consisting of a bond, $(C_1\text{-}C_8)$alkylene, $(C_2\text{-}C_8)$heteroalkylene, —C(O)—, —OC(O)—, —CH$_2$CO—, —CH$_2$SO— and —CH$_2$SO$_2$—.

In some embodiments, Q is —C(O)—.

W and Y each independently is a carbon or a heteroatom and W and Y are linked together to form a 5- or 6-membered cycloalkyl or cycloheteroalkyl ring, wherein the 5- or 6-membered ring is unsubstituted or substituted with halogen, NH$_2$, NO$_2$, $(C_1\text{-}C_{20})$alkyl, $(C_2\text{-}C_{20})$heteroalkyl, heteroaryl, aryl, heteroaryl$(C_1\text{-}C_6)$alkyl, heteroaryl$(C_2\text{-}C_6)$heteroalkyl, aryl$(C_1\text{-}C_6)$alkyl and aryl$(C_2\text{-}C_6)$heteroalkyl.

X is —CH$_2$—, SO$_2$ or —C(O)—.

In certain embodiments, X is —C(O)—.

$R^a$ is selected from the group consisting of —OR', =O, =NR', =N—OR', —NR'R", —SR', -halogen, —SiR'R"R'", —OC(O)R, —C(O)R, —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$.

$R^b$ is selected from the group consisting of —O', =O, =NR', =N—OR', —NR'R", —SR', -halogen, —SiR'R"R'", —OC(O)R', —C(O)R', —CO$_2$R, —CONR'R", —OC(O)

NR'R'', —NR''C(O)R', —NR'C(O)NR''R''', —NR''C(O)$_2$R', —NH—C(NH$_2$)=NH, —NR'C(NH$_2$)=NH, —NH—C(NH$_2$)=NR', —R', —S(O)R', —S(O)$_2$R, —S(O)$_2$NR'R'', —CN and —NO$_2$.

The subscript n is 0, 1, 2 or 3.

R', R'' and R''' each independently is H, unsubstituted (C$_1$-C$_8$)alkyl, heteroalkyl, unsubstituted aryl, or substituted aryl.

R$^1$ is heteroaryl or aryl.

In certain embodiments, R$^1$ is a unsubstituted or a meta- or para-substituted phenyl, wherein the substituent is a halogen, cyano, (C$_1$-C$_8$)alkyl, (C$_1$-C$_8$)heteroalkyl, (C$_1$-C$_8$)alkoxy, or (C$_1$-C$_8$)heteroalkoxy.

In certain embodiments, R$^1$ is

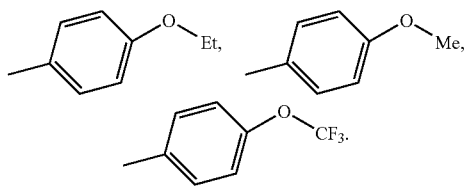

In some embodiments, R$^1$ is para-cyanophenyl.

R$^3$ is absent or is a member selected from the group consisting of —H, —CHR$^6$R$^7$, S(O)$_m$R$^5$, —S(O)$_m$N(R$^8$)R$^9$, —S(O)$_m$N(R$^8$)CH$_2$R$^6$, —N(R$^8$)SO$_2$R$^5$, —N(R$^8$)CH$_2$R$^{10}$,

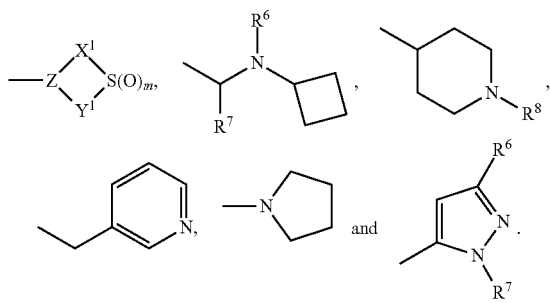

R$^4$ is a member selected from the group consisting of (C$_1$-C$_{20}$)alkyl, (C$_2$-C$_{20}$)heteroalkyl, heteroaryl, aryl, heteroaryl(C$_1$-C$_6$)alkyl, heteroaryl(C$_2$-C$_6$)heteroalkyl, aryl(C$_1$-C$_6$)alkyl and aryl(C$_2$-C$_6$)heteroalkyl.

In certain embodiments, -Q-R$^4$ is

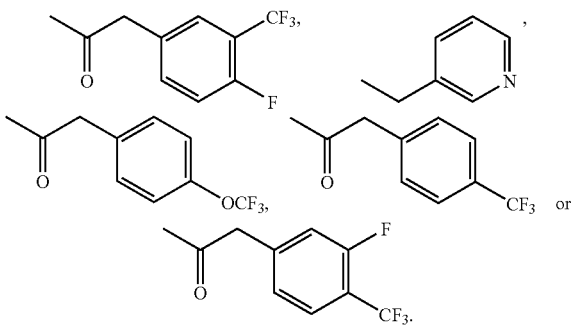

R$^5$ is selected from the group consisting of (C$_1$-C$_8$)alkyl, (C$_2$-C$_8$)heteroalkyl, aryl and heteroaryl.

R$^6$ and R$^7$ independently are hydrogen, (C$_1$-C$_8$)alkyl or (C$_2$-C$_8$)heteroalkyl.

R$^8$ is hydrogen, (C$_1$-C$_8$)alkyl, (C$_2$-C$_8$)heteroalkyl, heteroaryl or aryl.

R$^9$ is (C$_1$-C$_8$)alkyl.

R$^{10}$ is aryl.

In certain embodiments, the compound has the formula (IV):

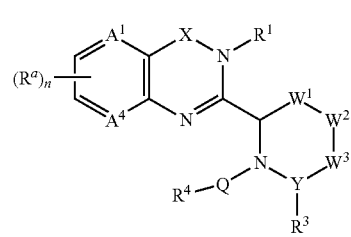

where R$^a$, R$^1$, R$^3$, R$^4$, A$^1$, A$^4$, Y, Q, X and subscript n are as defined above in formula III, and W$^1$, W$^2$ and W$^3$ are as defined below.

W$^1$ is absent or is selected from the group consisting of —O—, —S—, —S(O)—, —S(O)$_2$—, —C(O)—, —CH$_2$—, or —NR$^{11}$—.

In certain embodiments, W$^1$ is —CH$_2$—.

W$^2$ and Y independently are —CH$_2$—, —CHR$^{12}$—, —CH=, —CR$^{12}$=, —NH—, —N, or —NR$^{12}$—.

In certain embodiments, W$^2$ is —N=, —NH— or —N(CH$_3$)—.

W$^3$ is absent or is —O—, —S—, —S(O)—, —S(O)$_2$—, —CH$_2$—, —CHR$^{13}$—, —CH=, —CR$^{13}$=, —NH—, —N=, or —NR$^{13}$—.

In certain embodiments, W$^1$, W$^3$, and Y are each —CH$_2$—.

In certain embodiments, W$^1$ is —CH$_2$—, W$^2$ is —N=, W$^3$ is absent and Y is —CH= or —CR$^{12}$=.

In certain embodiments, W$^2$ is —N(CH$_3$)— or —NH—.

A$^1$ and A$^4$ independently are C(R$^b$) or N.

R$^{11}$ is selected from the group consisting of hydrogen, (C$_1$-C$_8$)alkyl, (C$_2$-C$_8$)heteroalkyl, aryl and heteroaryl.

R$^{12}$ and R$^{13}$ are independently (C$_1$-C$_{20}$)alkyl, (C$_2$-C$_{20}$)heteroalkyl, heteroaryl, aryl, heteroaryl(C$_1$-C$_6$)alkyl, heteroaryl(C$_2$-C$_6$)heteroalkyl, aryl(C$_1$-C$_6$)alkyl and aryl(C$_2$-C$_6$)heteroalkyl.

In certain embodiments, R$^1$ is para-cyanophenyl.

In some embodiments, the compound has the formula (V):

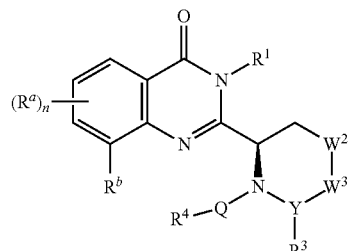

where R$^a$, R$^b$, R$^1$, R$^3$, R$^4$, Y, Q, W$^2$, W$^3$ and subscript n are defined as provided above.

It can be readily appreciated that the compounds of the invention exist in stereoisomers. In certain embodiments, the compound of formula (I) is a racemic compound. In some embodiments, the compound of formula (I) comprises a mixture of (S) and (R) enantiomers.

In some embodiments, the compound has the formula (Ia):

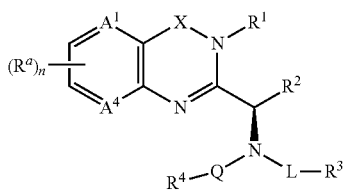

Ia where $R^a$, $R^1$, $R^2$, $R^3$, $R^4$, $A^1$, $A^4$, L, Q, X and subscript n are as defined above in formula I.

In other embodiments, the compound has the formula (Ib):

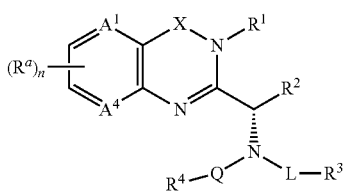

Ib where $R^a$, $R^1$, $R^2$, $R^3$, $R^4$, $A^1$, $A^4$, L, Q, X and subscript n are as defined above for formula I.

In further embodiments, the present invention provides a racemic mixture of compounds Ia and Ib.

In certain embodiments, the compound has the formula (IIa):

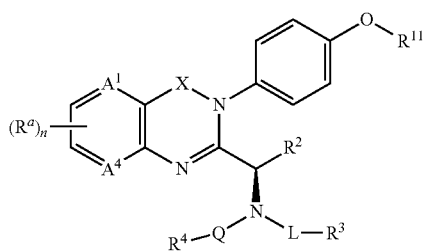

IIa where $R^a$, $R^2$, $R^3$, $R^4$, $R^{11}$, $A^1$, $A^4$, L, Q, X and subscript n are as described above in formula II.

In other embodiments, the compound has the formula (IIb):

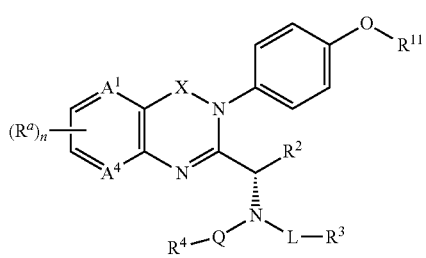

IIb where $R^a$, $R^2$, $R^3$, $R^4$, $R^{11}$, $A^1$, $A^4$, L, Q, X and subscript n are as described above in formula II.

In further embodiments, the present invention provides a racemic mixture of compounds IIa and IIb.

In certain embodiments, a compound of the present invention is in a solid form. For example, in some embodiments, a compound of the present invention is in a crystalline form. In some embodiments, the compound is in an amorphous form.

In certain embodiments, the compound of the present invention in a crystalline form has a purity of at least 80%, at least 90%, at least 92%, at least 95%, at least 97%, or at least 98%.

6.4 Preparation of the Compounds

Figure 2:
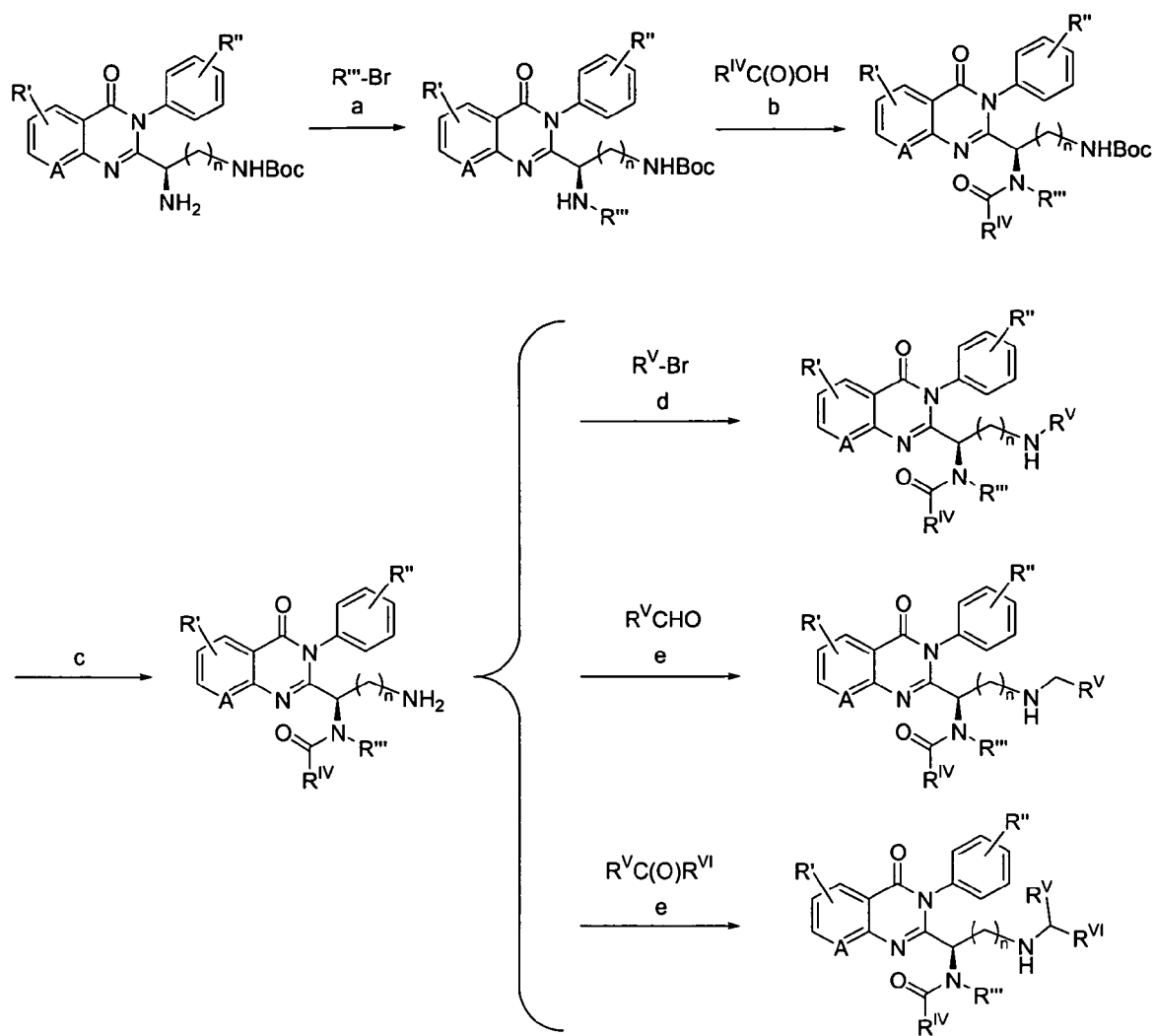
FIG. 2 illustrates a general synthesis scheme for preparation of compounds of the invention.
Figure 3:
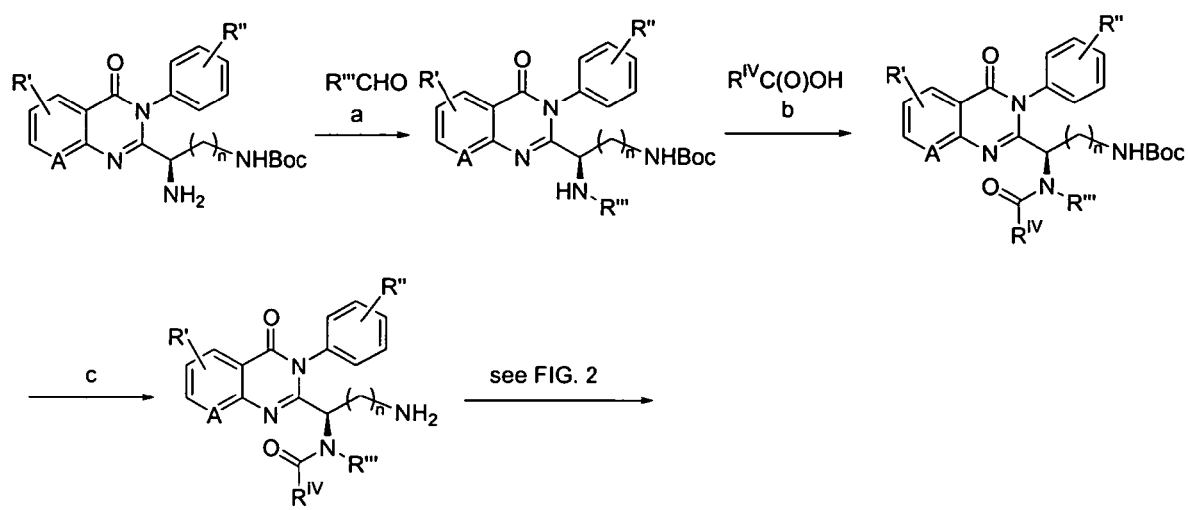
FIG. 3 illustrates a general synthesis scheme for preparation of compounds of the invention.

The compounds of the invention can be prepared by a variety of synthetic or semisynthetic techniques. FIGS. 1-3 and the Examples in Section 7 below provide a variety of synthesis routes to the compounds provided herein. Synthesis of appropriate starting materials can be prepared by techniques known or apparent to those of skill in the art or the starting materials may be commercially available. For instance, such materials can be prepared according to the methods of U.S. Patent Applications Nos. 2002/0160159 A1 and 2003/0055054 A1 and International Publication No. WO 02/83143, the contents of which are each hereby incorporated by reference in its entirety.

For example, compounds of the invention can be prepared according to the following scheme, or modified versions thereof apparent to one of skill in the art:

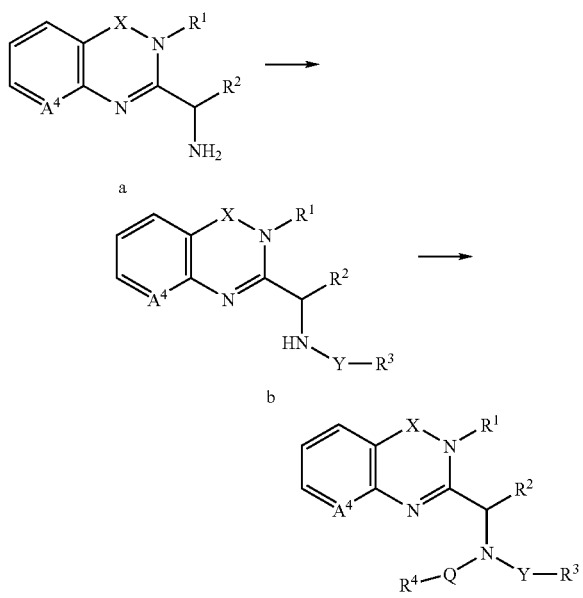

In the above scheme, the product c can be prepared from starting material a, prepared for example according to WO 02/83143, using techniques and reactants apparent to those of skill in the art. For instance, to create intermediate b, starting material a can be reacted with a activated derivative of (—Y—$R^3$). In turn, to created product c, intermediate b can be reacted with an activated derivative of (Q-$R^4$). Numerous exemplary syntheses of compounds of the invention are provided in the examples below including starting materials, reactants, reaction conditions, intermediates and products. Further methods of preparing the compounds of the invention will be apparent from the above scheme, the exemplary schemes in the examples below and the teachings herein.

One of skill in the art will appreciate that the substituents can be added or altered before, during or after preparation of the heterocyclic scaffolding and that suitable adjustments in conditions (e.g., temperatures, solvents, etc.) can be made. Additionally, one of skill in the art will recognize that protecting groups may be necessary for the preparation of certain compounds and will be aware of those conditions compatible with a selected protecting group.

The exemplary methods and the examples described herein are illustrative of the present invention and are not to be construed as limiting the scope thereof.

6.5 Compositions

In another aspect, the present invention provides pharmaceutical compositions for modulating chemokine receptor activity in humans and animals. The compositions comprise a compound of the present invention with a pharmaceutically acceptable carrier or diluent.

"Modulation" or modulating of chemokine receptor activity, as used herein in its various forms, is intended to encompass antagonism, agonism, partial antagonism and/or partial agonism of the activity associated with a particular chemokine receptor, preferably the CXCR3 receptor. The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,166,452 and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

For topical use, creams, ointments, jellies, solutions or suspensions, etc., containing the compounds of the present invention are employed. As used herein, topical application is also meant to include the use of mouth washes and gargles.

The pharmaceutical composition and method of the present invention may further comprise other therapeutically effective compounds as noted herein which are usually applied in the treatment or prevention of the above mentioned pathological conditions.

6.6 Methods of Use

In another aspect, the present invention provides methods of treating CXCR3-mediated conditions or diseases by administering to a subject having such a disease or condition, a therapeutically effective amount of compound or composition of the invention. The "subject" is defined herein to include animals such as mammals, including, but not limited to, primates (e.g., humans), cows, sheep, goats, horses, pigs, dogs, cats, rabbits, rats, mice and the like.

As used herein, the phrase "CXCR3-mediated condition or disease" and related phrases and terms refer to a condition characterized by inappropriate, e.g., less than or greater than normal, CXCR3 activity. Inappropriate CXCR3 activity might arise as the result of CXCR3 expression in cells which normally do not express CXCR3, increased CXCR3 expression (leading to, e.g., inflammatory and immunoregulatory disorders and diseases), or, decreased CXCR3 expression (leading to, e.g., certain cancers and angiogenic and vasculogenic-related disorders). Inappropriate CXCR3 functional activity might arise as the result of CXCR3 expression in cells which normally do not express CXCR3, increased CXCR3 expression (leading to, e.g., inflammatory and immunoregulatory disorders and diseases) or decreased CXCR3 expression. Inappropriate CXCR3 functional activity might also arise as the result of chemokine secretion by cells which normally do not secrete a CXC chemokine, increased chemokine expression (leading to, e.g., inflammatory and immunoregulatory disorders and diseases) or decreased chemokine expression. A CXCR3-mediated condition or disease may be completely or partially mediated by inappropriate CXCR3 functional activity. However, a CXCR3-mediated condition or disease is one in which modulation of CXCR3 results in some effect on the underlying condition or disease (e.g., a CXCR3 antagonist results in some improvement in patient well-being in at least some patients).

The term "therapeutically effective amount" means the amount of the subject compound that will elicit the biological or medical response of a tissue, system, animal or human that is being sought by the researcher, veterinarian, medical doctor or other clinician or that is sufficient to prevent development of or alleviate to some extent one or more of the symptoms of the disease being treated.

Diseases and conditions associated with inflammation, infection and cancer can be treated with the present compounds and compositions. In one group of embodiments, diseases or conditions, including chronic diseases, of humans or other species can be treated with inhibitors of CXCR3 function. These diseases or conditions include: (1) inflammatory or allergic diseases such as systemic anaphylaxis or hypersensitivity responses, drug allergies, insect sting allergies and food allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; asthma and respiratory allergic diseases such as allergic rhinitis, hypersensitivity lung diseases, and the like, (2) autoimmune diseases, such as arthritis (rheumatoid and psoriatic), multiple sclerosis, systemic lupus erythematosus, type I diabetes, glomerulonephritis, and the like, (3) graft rejection (including allograft rejection and graft-v-host disease) and conditions associated therewith, and (4) other diseases in which undesired inflammatory responses are to be inhibited, e.g., atherosclerosis, myositis, neurodegenerative diseases (e.g., Alzheimer's disease), encephalitis, meningitis, hepatitis, nephritis, sepsis, sarcoidosis, conjunctivitis, otitis, chronic obstructive pulmonary disease, sinusitis and Behcet's syndrome. In another group of embodiments, diseases or conditions are treated with agonists of CXCR3 function. Examples of diseases to be treated with CXCR3 agonists include cancers, diseases in which angiogenesis or neovascularization play a role (neoplastic diseases, retinopathy and macular degeneration), infectious diseases and immunosuppressive diseases.

Preferably, the present methods are directed to the treatment or prevention of diseases or conditions selected from neurodegenerative diseases (e.g., Alzheimer's disease), multiple sclerosis, systemic lupus erythematosus, rheumatoid arthritis, atherosclerosis, encephalitis, meningitis, hepatitis, nephritis, sepsis, sarcoidosis, psoriasis, eczema, uticaria, type I diabetes, asthma, conjunctivitis, otitis, allergic rhinitis, chronic obstructive pulmonary disease, sinusitis, dermatitis, inflammatory bowel disease, ulcerative colitis, Crohn's disease, Behcet's syndrome, gout, cancer, viral infections (e.g., HIV), bacterial infections, and organ transplant conditions or skin transplant conditions. The term "organ transplant conditions" is meant to include bone marrow transplant conditions and solid organ (e.g., kidney, liver, lung, heart, pancreas or combination thereof) transplant conditions.

Diseases or conditions that can be treated with the present compounds and compositions include diseases commonly associated with (1) inflammatory or allergic diseases, (2) autoimmune diseases, (3) graft rejection and (4) other diseases in which undesired inflammatory responses are to be inhibited, as described above. For example, restenosis following a procedure such as balloon angioplasty, is commonly associated with atherosclerosis and can be treated with the present compounds and compositions.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention can be combined with other compounds having related utilities to treat or prevent inflammatory and immune disorders and diseases, including asthma and allergic diseases, as well as autoimmune pathologies such as rheumatoid arthritis and atherosclerosis, and those pathologies noted above. In many instances, compositions which include a compound of the invention and an alternative or second therapeutic agent have additive or synergistic effects when administered.

For example, in the treatment or prevention of inflammation, the present compounds may be used in conjunction or combination with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextromethorphan; a diuretic; and a sedating or non-sedating antihistamine. Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists, (b) steroids such as beclomethasone, methylprednisolone, betamethasone, prednisone, dexamethasone, and hydrocortisone; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal anti-inflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib (Celebrex®) and rofecoxib (Vioxx®); (h) inhibitors of phosphodiesterase type IV (PDE-IV); (i) gold compounds such as auranofin and aurothioglucose, (j) inhibitors of phosphodiesterase type IV (PDE-IV); (k) other antagonists of the chemokine receptors, especially CCR1, CCR2, CCR3, CCR5, CCR6, CCR8 and CCR10; (l) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (m) anti-diabetic agents such as insulin, sulfonylureas, biguamides (metformin), α-glucosidase inhibitors (acarbose) and glitazones (troglitazone and pioglitazone); (n) preparations of interferon beta (interferon β-1α, interferon β-1β); (O) etanercept (Enbrel®), (p) antibody therapies such as orthoclone (OKT3), daclizumab (Zenapax®), infliximab (Remicade®), basiliximab (Simulect®) and anti-CD40 ligand antibodies (e.g., MRP-1); and (q) other compounds such as 5-aminosalicylic acid and prodrugs thereof, hydroxychloroquine, D-penicillamine, antimetabolites such as azathioprene and 6-mercaptopurine, and cytotoxic cancer chemotherapeutic agents. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Immunosuppressants within the scope of the present invention further include, but are not limited to, leflunomide, RAD001, ERL080, FTY720, CTLA-4, antibody therapies such as orthoclone (OKT3), daclizumab (Zenapax®) and basiliximab (Simulect®), and antithymocyte globulins such as thymoglobulins.

In particularly preferred embodiments, the present methods are directed to the treatment or prevention of multiple sclerosis using a compound of the invention either alone or in combination with a second therapeutic agent selected from betaseron, avonex, azathioprene (Imurek®, Imuran®), capoxone, prednisolone and cyclophosphamide. When used in combination, the practitioner can administer a combination of the therapeutic agents, or administration can be sequential.

In still other particularly preferred embodiments, the present methods are directed to the treatment or prevention of rheumatoid arthritis, wherein the compound of the invention is administered either alone or in combination with a second therapeutic agent selected from the group consisting of methotrexate, sulfasalazine, hydroxychloroquine, cyclosporine A, D-penicillamine, infliximab (Remicade®), etanercept (Enbrel®), auranofin and aurothioglucose.

In yet other particularly preferred embodiments, the present methods are directed to the treatment or prevention of an organ transplant condition wherein the compound of the invention is used alone or in combination with a second therapeutic agent selected from the group consisting of cyclosporine A, FK-506, rapamycin, mycophenolate, prednisolone, azathioprene, cyclophosphamide and an antilymphocyte globulin.

7. EXAMPLES

Reagents and solvents used below can be obtained from commercial sources such as Aldrich Chemical Co. (Milwaukee, Wis., USA). $^1$H-NMR spectra were recorded on a Bruker 500 MHZ NMR spectrometer. Significant peaks are tabulated in the order: number of protons, multiplicity (s, singlet; d, doublet; t, triplet; q, quartet; m, multiplet; br s, broad singlet) and coupling constant(s) in Hertz (Hz). Electrospray ionization (ESI) mass spectrometry analysis was conducted on a Hewlett-Packard 1100 MSD electrospray mass spectrometer using the HP1 100 HPLC for sample delivery. Mass spectrometry results are reported as the ratio of mass over charge. Each compound was dissolved in methanol at 0.1 mg/mL and 1 microliter was infused with the delivery solvent into the mass spectrometer, which scanned from 100 to 1500 daltons. Each compound could be analyzed in the positive ESI mode, using 1:1 acetonitrile/water with 1% acetic acid as the delivery solvent. Each compound could also be analyzed in the negative ESI mode, using 2 mM NH$_4$OAc in acetonitrile/water as delivery solvent.

7.1 Example 1

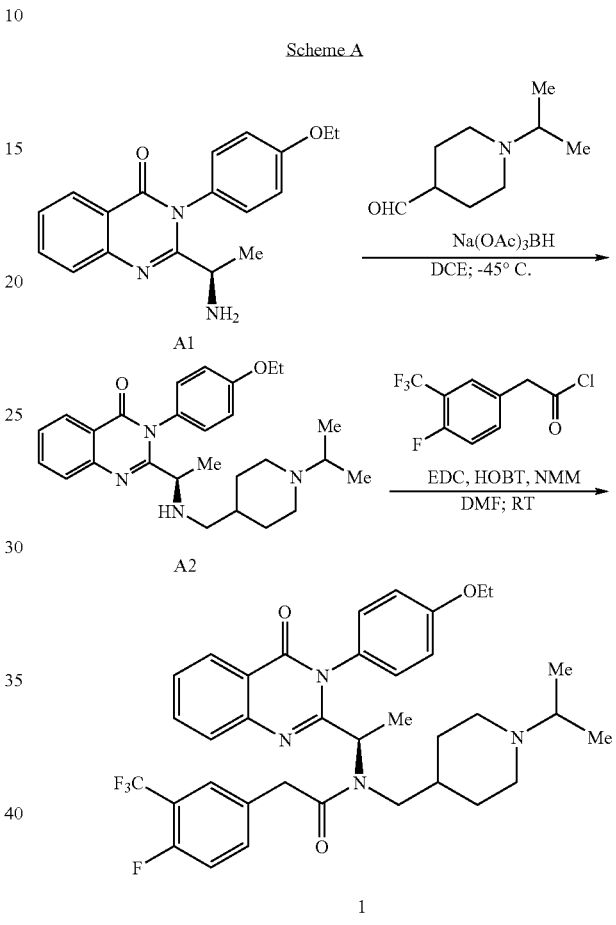

Compound 1 was synthesized from A1 in two steps as outlined in Scheme A.

The compound A1 was synthesized as outlined in International Publication No. WO 02/83143, Scheme 3, page 77, which is incorporated herein by reference in its entirety for all purposes.

(R)-3-(4-Ethoxy-phenyl)-2-{1-[(1-isopropyl-piperidin-4-ylmethyl)-amino]-ethyl}-3H-quinazolin-4-one (A2). To a solution of 18.7 g 1-isopropyl-piperidine-4-carbaldehyde (0.12 mol, 1.00 equiv.) dissolved in 300 mL 1,2-dichloroethane cooled to −45° C. internal temperature was added 37.3 g A1 (0.12 mol, 1.00 equiv.) in three equivalent portions at 5 min. intervals. The mixture was stirred at −45° C. for 15 min. then 39 g sodium triacetoxyborohydride (0.18 mol, 1.50 equiv.) was added in three equivalent portions at 5 min. intervals. The reaction mixture was allowed to equilibrate slowly from −45° C. to room temperature overnight. Saturated aqueous sodium bicarbonate solution was added until aqueous layer pH=9-10. The separated aqueous layer was extracted twice with dichloromethane. The combined organic layers were dried over magnesium sulfate, filtered and concentrated in vacuo to afford A2 as a glassy solid, which was used without further purification. ¹H NMR (400 MHz; CDCl₃; T=298.1 K) δ 1.01 (d, J=6.6 Hz, 6H), 1.11-1.29 (m, 2H), 1.23 (d, J=6.6 Hz, 3H), 1.11-1.41 (m, 1H), 1.46 (t, J=6.9 Hz, 3H), 1.72 (dd, J=14.2, 33.2 Hz, 2H), 1.98-2.20 (m, 3H), 2.20-2.37 (m, 2H), 2.58-2.73 (m, 1H), 2.78-2.92 (m, 2H), 3.43 (dd, J=7.6, 7.6 Hz, 1H), 4.10 (qt, J=6.9 Hz, 2H), 6.97-7.08 (m, 2H), 7.08-7.18 (m, 2H), 7.46 (dd, J=8.5, 8.5 Hz, 1H), 7.69 (d, J=8.5 Hz, 1H), 8.27 (d, J=8.5 Hz, 1H) ppm.

(R)—N-{1-[3-(4-Ethoxy-phenyl)-4-oxo-3,4-dihydro-quinazolin-2-yl]-ethyl}-2-(4-fluoro-3-trifluoromethyl-phenyl)-N-(1-isopropyl-piperidin-4-ylmethyl)-acetamide (1). To a mixture of 49.3 g A2 (0.11 mol, 1.00 equiv.) and 29.3 g 4-fluoro-3-(trifluoromethyl)phenylacetic acid (0.13 mol, 1.20 equiv.) in 120 mL N,N-dimethylformamide, DMF, and 40 mL dichloromethane at room temperature was added 12 mL N-methylmorpholine, NMM (0.11 mol, 1.00 equiv.) and 14.9 g 1-hydroxybenzotriazole, HOBT (0.11 mol, 1.00 equiv.). To the solution was added 1-(3-dimethylaminopropyl)-3-ethylcarbodiimide hydrochloride, EDC (0.22 mol, 2.00 equiv.) in two equivalent portions at a 5 min. interval. The reaction mixture was stirred at room temperature for 16 h then taken-up in 800 mL ethyl acetate and washed with saturated aqueous sodium bicarbonate and aqueous brine six times. The organic extract was dried over magnesium sulfate, filtered and concentrated in vacuo to afford a glassy solid. The product was purified by recrystallization from diethyl ether to yield 41 g of 1 as a colorless solid. ¹H NMR (400 MHz; d₆-DMSO; T=393 K): δ 0.92 (d, J=6.6 Hz, 6H), 0.95-1.20 (m, 2H), 1.35 (t, J=7.0 Hz, 3H), 1.32-1.50 (m, 2H), 1.50 (d, J=6.6 Hz, 3H), 1.58 (d, J=1.0 Hz, 1H), 1.85 (dd, J=10.3, 10.3 Hz, 1H), 1.99 (dd, J=11.4, 11.4 Hz, 1H), 2.52-2.68 (m, 2H), 2.75 (d, J=11.4 Hz, 1H), 2.88 (br s, 1H), 3.10 (dd, J=9.1, 14.8 Hz, 1H), 3.30 (dd, J=9.1, 13.7 Hz, 1H), 3.52 (br s, 1H), 4.09 (qt, J=7.0 Hz, 2H), 5.12 (qt, J=9.12 Hz, 1H), 7.00-7.13 (m, 2H), 7.18 (d, J=10.3 Hz, 1H), 7.30 (dd, J=10.3, 10.3 Hz, 1H), 7.33-7.48 (m, 3H), 7.57 (dd, J=9.5, 9.5 Hz, 1H), 7.72 (d, J=9.5 Hz, 1H), 7.87 (dd, J=9.5, 9.5 Hz, 1H), 8.15 (d, J=7.8 Hz, 1H) ppm; MS (ESI⁺) m/z=653.3 [M+H]⁺; Analytical calculated: 66.24%, C, 6.18% H, 11.64% F and 8.58% N. Found: 66.17% C, 6.05% H, 8.56% N, 11.59% F.

TABLE 1

Examples 2-11

| Example | X | R¹ | R² |
|---|---|---|---|
| 2 | =N— | —OCH₂CF₃ | —CH₂—SO₂Et |
| 3 | =N— | —OCH₂CF₃ | —CH₂—SO₂Me |
| 4 | =N— | —OCH₂CF₃ | 4-(tetrahydrothiopyranyl) |
| 5 | =N— | —OCH₂CF₃ | 4-(tetrahydrothiopyranyl-1,1-dioxide) |
| 6 | =N— | —OEt | —CH₂—SO₂Ph |
| 7 | =N— | —OEt | 4-(tetrahydrothiopyranyl) |
| 8 | =N— | —OEt | 4-(tetrahydrothiopyranyl-1,1-dioxide) |
| 9 | =N— | —OEt | —CH₂—SO₂Et |
| 10 | =CH— | —OEt | —CH₂—SO₂Et |
| 11 | =CH— | —OCH₂CF₃ | —CH₂—SO₂Et |

7.2 Example 2

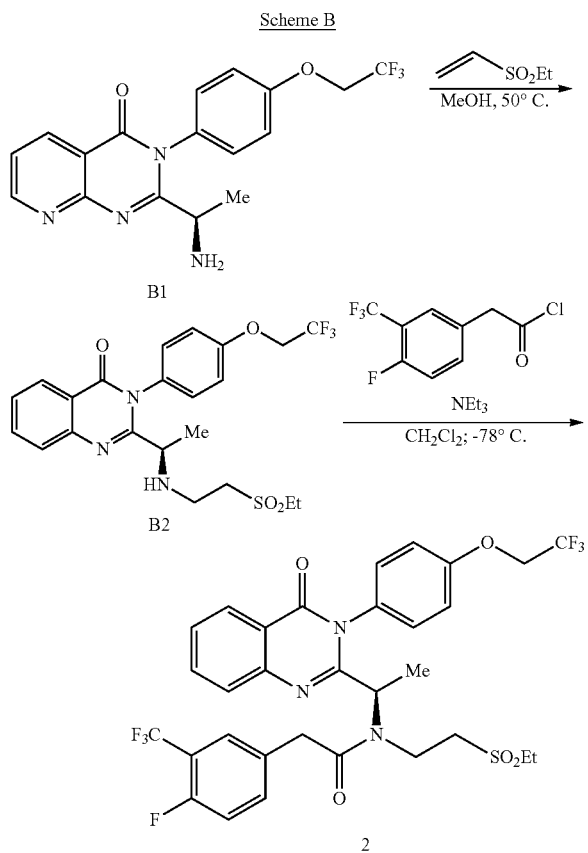

The compound B1 was synthesized as outlined in International Publication No. WO 02/83143, Scheme 9, page 91, substituting 4-(2,2,2-trifluoroethoxy)aniline for p-phenetidine in step 3. Compound 2 was synthesized from B1 in two steps as shown in Scheme B.

(R)-2-[1-(2-Ethanesulfonyl-ethylamino)-ethyl]-3-[4-(2,2,2-trifluoroethoxy)-phenyl]-3H-pyrido[2,3-d]pyrimidin-4-one (B2). A mixture of 2.18 g B1 (5.98 mmol, 1.00 equiv.) and 687 µL ethyl vinyl sulfone (6.58 mmol, 1.10 equiv.) in 10 mL methanol was stirred overnight in a 50° C. oil bath then concentrated in vacuo. The product B2 was used without further purification in the next step. MS (ESI+) m/z=485.1 [M+H]+.

(R)—N-(2-Ethanesulfonyl-ethyl)-2-(4-fluoro-3-trifluoromethyl-phenyl)-N-(1-{4-oxo-3-[4-(2,2,2-trifluoroethoxy)-phenyl]-3,4-dihydro-pyrido[2,3-d]pyrimidin-2-yl}-ethyl)-acetamide (2). The acid chloride (4-fluoro-3-trifluoromethyl-phenyl)acetyl chloride was prepared by addition of several drops of DMF to an ice-cold solution of 2.06 g (4-fluoro-3-trifluoromethyl-phenyl)acetic acid (9.27 mmol, 1.70 equiv.) and 0.81 mL oxalyl chloride (9.27 mmol, 1.70 equiv.) dissolved in 15 mL dichloromethane. Gas evolution ensued and the reaction was equilibrated to room temperature and stirred for 2 h until gas evolution ceased. This solution was added dropwise over 15 min. to a solution of 2.6 g B2 (5.37 mmol, 1.00 equiv.) and 2.24 mL triethylamine (16.1 mmol, 3.00 equiv.) dissolved in 20 mL dichloromethane cooled by an acetone-dry ice bath. The resulting mixture was stirred at low temperature for 20 min. then poured into saturated aqueous sodium bicarbonate. The organic separation was washed with brine, dried over magnesium sulfate, filtered, and concentrated in vacuo to afford a glassy solid. The product was purified by chromatography on silica gel, eluting with a gradient of 50% ethyl acetate in hexane to 100% ethyl acetate. The chromatographed product was then recrystallized from methyl tert-butyl ether to afford 2 as colorless crystals, m.p.=157-159° C. $^1$H NMR (400 MHz; CDCl$_3$; T=300 K) {mixture of S-cis:S-trans amide rotamers in ca. 2.3:1 ratio} δ 1.20 (t, J=7.6 Hz, 3H), 1.46 (t, J=7.2 Hz, 6.5H), 1.46 (d, J=7.2 Hz, 6.5H), 2.48 (d, J=16 Hz, 1H), 2.92 (ddd, J=2.8, 7.6, 16.0 Hz, 2H), 2.94 (d, J=16 Hz, 1H), 3.13 (ddd, J=3.6, 7.2, 14.8 Hz, 4.6H), 3.22 (dd, J=6.8, 6.8 Hz, 2H), 3.50 (ddd, J=5.2, 10.6, 13.3 Hz, 2.3H), 3.67 (ddd, J=8.0, 8.0, 13.3 Hz, 1H), 3.84 (s, 4.6H), 3.90 (ddd, J=4.8, 10, 14.8 Hz, 2.3H), 4.02 (ddd, J=8.0, 8.0, 13.3 Hz, 1H), 4.06-4.27 (m, 4.6H), 4.42 (qt, J=8 Hz, 6.6H), 5.01 (qt, J=6.8 Hz, 1H), 5.16 (qt, J=7.2 Hz, 2.3H), 7.09-7.19 (m, 10H), 7.21-7.28 (m, 5H), 7.33-7.50 (m, 8.9H), 7.53 (dd, J=4.6, 9.1 Hz, 1H), 7.63-7.68 (m, 2.3H), 8.58 (dd, J=2.0, 8.0 Hz, 2.3H), 8.61 (dd, J=2.0, 8.0 Hz, 1H), 8.96 (dd, J=2.0, 4.4 Hz, 2.3H), 9.06 (dd, J=2.0, 4.8 Hz, 1H) ppm. MS (ESI+) m/z=688.9 [M+H]+. Analytical calculated: 52.33% C, 3.95% H, 19.31% F, 8.14% N. Found: 52.29% C, 3.97% H, 19.40% F, 8.12% N.

7.3 Example 3

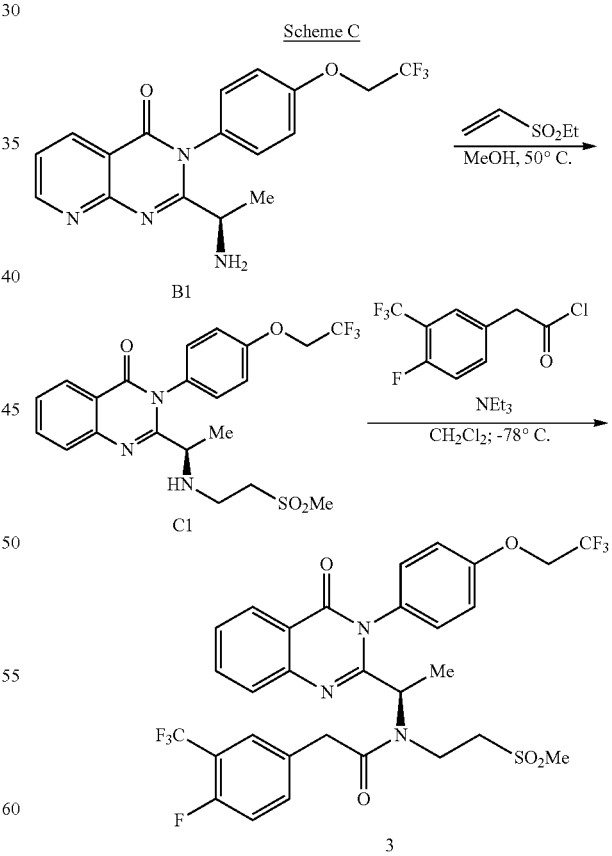

(R)-2-(4-fluoro-3-trifluoromethyl-phenyl)-N-(2-methanesulfonyl-ethyl)-N-(1-{4-oxo-3-[4-(2,2,2-trifluoroethoxy)-phenyl]-3,4-dihydro-pyrido[2,3-d]pyrimidin-2-yl}-ethyl)-acetamide (3). Compound 3 was synthesized in two steps from B1 following the previously described synthetic sequence for 2, substituting methyl vinyl sulfone for ethyl vinyl sulfone in the first step. $^1$H NMR: a mixture of cis/trans amide rotamers in ca. 2.0:1 ratio (400 MHz; CDCl$_3$; T=298 K) $\delta_{major}$ 8.98 (dd, J=4.46, 1.78 Hz, 1H), 8.62 (dd, 7.69, 1.78 Hz, 1H), 7.66 (dd, J=9.71, 3.33 Hz, 1H), 7.10-7.46 (m, 7H), 5.14 (q, J=7.26 Hz, 1H), 4.41 (q, J=7.94 Hz, 2H), 3.64-4.24 (m, 5H), 3.10 (s, 3H), 2.47 (m, 1H), 1.46 (d, J=7.2 Hz, 3H) and $\delta_{minor}$ 9.06 (m, 1H), 8.63 (obscured dd, J=7.28, 1.63 Hz, 1H), 5.01 (q, J=6.64 Hz, 1H), 2.83 (s, 3H), 1.58 (d, J=6.71 Hz, 3H) ppm. MS (ESI+) 675 [M+H]+.

7.4 Examples 4 and 5

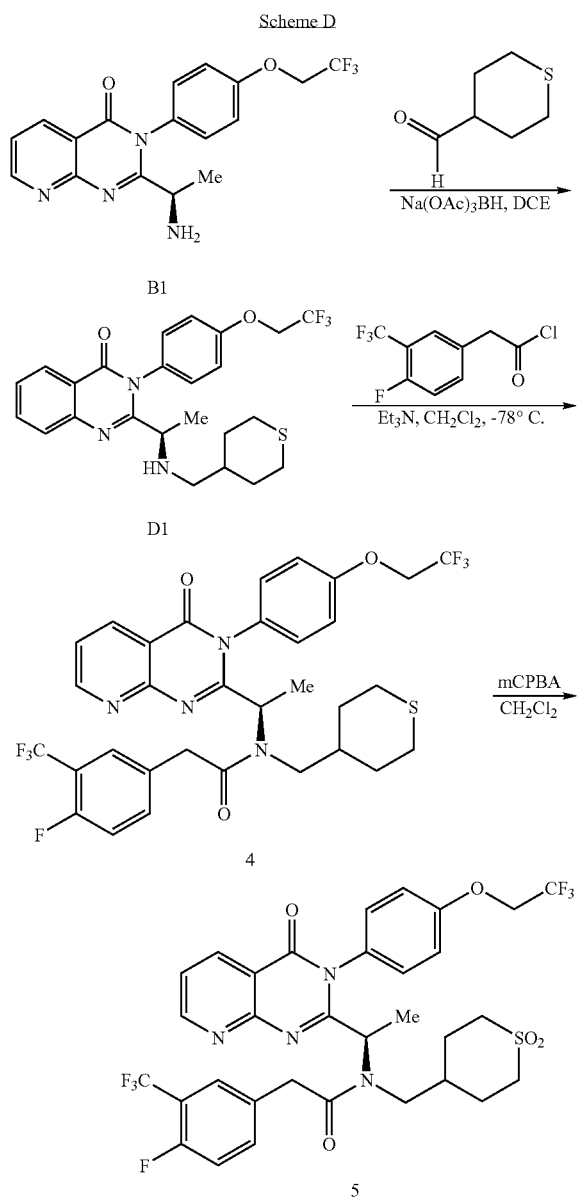

Compounds 4 and 5 were synthesized from previously described B1 in two and three steps respectively, as shown in Scheme D.

(R)-2-{1-[(Tetrahydro-thiopyran-4-ylmethyl)-amino]-ethyl}-3-[4-(2,2,2-trifluoro-ethoxy)-phenyl]-3H-pyrido[2,3-d]pyrimidin-4-one (D1). Previously described B1 (159 mg, 0.44 mmol), tetrahydrothiopyranyl-4-carboxaldehyde (70 µL, 0.53 mmol), and sodium triacetoxyborohydride (277 mg, 1.32 mmol) were stirred in 1,2-dichloroethane at room temperature for 1 h. The reaction mixture was diluted with dichloromethane, then washed with saturated aqueous sodium bicarbonate and brine. The organic layer was dried over anhydrous magnesium sulfate, filtered, and concentrated in vacuo, to afford 208 mg of D1, which was carried forward without purification.

(R)-2-(4-Fluoro-3-trifluoromethyl-phenyl)-N-(1-{4-oxo-3-[4-(2,2,2-trifluoro-ethoxy)-phenyl]-3,4-dihydro-pyrido[2,3-d]pyrimidin-2-yl}-ethyl)-N-(tetrahydro-thiopyran-4-ylmethyl)-acetamide (4). The compound 4-fluoro-3-trifluoromethylphenylacetic acid (164 mg, 0.74 mmol) was dissolved in dichloromethane and cooled to 0° C. Oxalyl chloride (64 µL, 0.74 mmol) was added, then after 5 min, N,N-dimethylformamide (5.7 µL, 0.07 mmol) was added. The reaction stirred at 0° C. for 30 min. and room temperature for 1 h. The solution was added slowly to a mixture of D1 (208 mg, 0.43 mmol) and triethylamine (182 µL, 1.30 mmol) in dichloromethane at −78° C. The mixture was stirred for 30 min., then washed with saturated aqueous sodium bicarbonate and brine. The organic extract was dried over anhydrous magnesium sulfate, filtered, and concentrated in vacuo. The resulting product was purified by chromatography (2% methanol with 0.1% ammonium hydroxide in dichloromethane), yielding 265 mg of 4.

(R)—N-(1,1-Dioxo-hexahydro-1$\lambda^6$-thiopyran-4-ylmethyl)-2-(4-fluoro-3-trifluoromethyl-phenyl)-N-(1-{4-oxo-3-[4-(2,2,2-trifluoro-ethoxy)-phenyl]-3,4-dihydro-pyrido[2,3-d]pyrimidin-2-yl}-ethyl)-acetamide (5). Compound 4 (265 mg, 0.39 mmol) was dissolved in dichloromethane and cooled to 0° C. To this solution was added 3-chloroperoxybenzoic acid (77%, 174 mg, 0.78 mmol) and the mixture was equilibrated to room temperature overnight. The reaction was washed twice with 10% aqueous sodium thiosulfate, and once with brine. The organic layer was then dried over anhydrous magnesium sulfate, filtered, and concentrated in vacuo. The product was purified by chromatography (3% methanol with 0.1% ammonium hydroxide in dichloromethane), recovering 136 mg of 5. MS (MH+): 688.2. $^1$H NMR (500 MHz; CDCl$_3$; T=298 K): δ 8.30 (t, 1H, J=7.9 Hz), 7.86 (m, 1H), 7.69-7.35 (m, 4H), 7.25 (m, 2H), 7.13 (m, 3H), 5.23-4.93 (dq, 1H, J=7.2, 143 Hz), 4.43 (quint, 2H, J=8.0 Hz), 4.22-3.58 (m, 2H), 3.26 (m, 1H), 3.06-2.97 (m, 3H), 1.55 (d, 2H, J=6.7 Hz), 1.43 (dt, 3H, J=7.6, 2.0 Hz), 1.32 (t, 3H, J=7.5 Hz) ppm.

7.5 Example 6

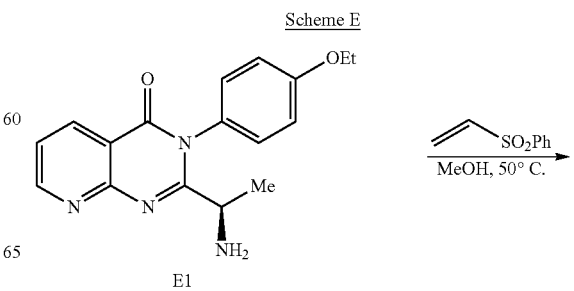

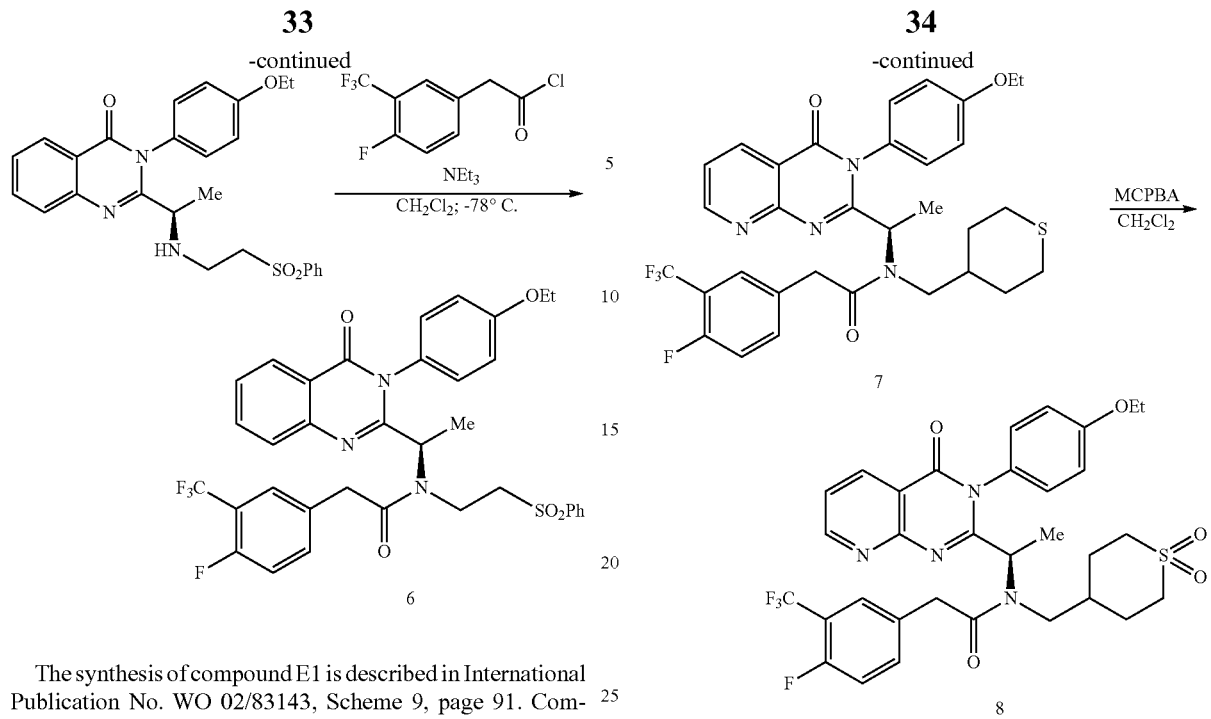

The synthesis of compound E1 is described in International Publication No. WO 02/83143, Scheme 9, page 91. Compound 6 was synthesized from E1 in two steps.

(R)—N-(2-benzenesulfonyl-ethyl)-N-{1-[3-(4-ethoxy-phenyl)-4-oxo-3,4-dihydro-pyrido[2,3-d]pyrimidin-2-yl]-ethyl}-2-(4-fluoro-3-trifluoromethyl-phenyl)-acetamide (6). Compound 6 was synthesized in two steps from E1 following the synthetic sequence for 2, substituting phenyl vinyl sulfone for ethyl vinyl sulfone in step 1. $^1$H NMR: a mixture of cis/trans amide rotamers in ca. 2.0:1 ratio (400 MHz, CDCl$_3$; T=25° C.) $\delta_{major}$ 8.98 (dd, J=4.63, 1.94 Hz, 1H), 8.61 (d, J=7.97, 1.80 Hz, 1H), 7.98 (d, J=7.43 Hz, 1H), 7.01-7.75 (m, 12H), 5.14 (q, J=7.20 Hz, 1H), 4.07 (m, 2H), 2.86-3.90 (m, 6H), 1.45 (obscured t, J=6.93 Hz, 3H), 1.34 (d, J=7.23 Hz, 3H) and $\delta_{minor}$ 9.09 (dd, J=4.3, 1.84 Hz, 1H), 8.64 (dd, J=7.88, 1.87 Hz, 1H), 1.54 (d, J=6.73 Hz, 3H), 1.44 (obscured t, J=6.74 Hz, 3H). MS (ESI+) 683 [M+H]$^+$.

7.6 Examples 7 and 8

Scheme F

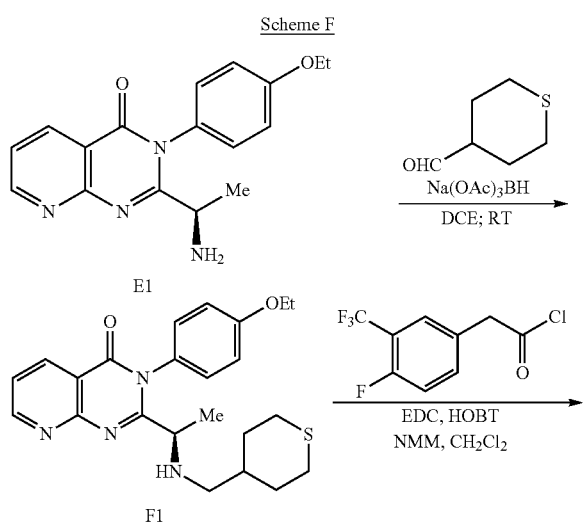

The compounds 7 and 8 were synthesized in two and three steps respectively from the previously described E1.

(R)-3-(4-ethoxy-phenyl)-2-{1-[(tetrahydro-thiopyran-4-ylmethyl)-amino]-ethyl}-3H-pyrido[2,3-d]pyrimidin-4-one (F1). To a mixture of E1 (531 mg, 1.71 mmol) and tetrahydro-thiopyran-4-carbaldehyde (234 mg, 1.79 mmol) in 9 mL of 1,2-dichloroethane was added 1.09 g (5.13 mmol) of sodium triacetoxyborohydride at room temperature. The resulting mixture was allowed to stir at room temperature for 3 h. Upon completion, 25 mL of saturated aqueous sodium bicarbonate solution was added, and the resulting mixture was extracted with dichloromethane (30 mL×3). The combined extracts were washed with water and brine, dried over anhydrous sodium sulfate and concentrated in vacuo. The residue was dried under vacuum to give 550 mg of desired product F1, which was used in next step without further purification. MS (ESI$^+$) 425 [M+H]$^+$.

(R)—N-{1-[3-(4-Ethoxy-phenyl)-4-oxo-3,4-dihydro-pyrido[2,3-d]pyrimidin-2-yl]-ethyl}-2-(4-fluoro-3-trifuorom-ethyl-phenyl)-N-(tetrahydro-thiopyran-4-ylmethyl)-aceta-mide (7). A mixture of F1 (550 mg, 1.29 mmol), 4-fluoro-3-trifluoromethylphenyl acetic acid (374 mg, 1.68 mmol), EDC (371 mg, 1.93 mmol), HOBT (198 mg, 1.29 mmol) and 300 µL (2.58 mmol) of NMM in 13 mL of dichloromethane was allowed to stir at room temperature for 3 days. Upon completion, the mixture was concentrated and 15 mL of water was added. The resulting mixture was extracted with ethyl acetate (30 mL×3). The combined extracts were washed with water and brine, dried over anhydrous sodium sulfate and concentrated. The material was purified by chromatography on a silica gel column using 50% and 80% of ethyl acetate/hexane successively as the eluents to give 531 mg of product 7. $^1$H NMR for a mixture of cis/trans amide rotamers in ca. 2:1 ratio (400 MHz, CDCl$_3$; T=25° C.) $\delta_{major}$ 8.96 (dd, J=4.58, 2.01 Hz, 1H), 8.56 (dd, J=7.87, 2.02 Hz, 1H), 7.0-7.55 (m, 8H), 5.16 (q, J=7.21 Hz, 1H), 4.05 (q, J=6.92 Hz, 2H), 1.44 (obscured d, J=7.19 Hz, 3H), 1.43 (obscured t, J=6.96 Hz, 3H) and $\delta_{minor}$ 9.06 (dd, J=4.56, 1.96 Hz, 1H), 8.63 (dd, J=7.90, 1.96 Hz, 1H), 5.02 (q, J=6.81 Hz, 1H), 1.58 (d, J=6.74 Hz, 3H). MS (ESI+) 629 [M+H]$^+$.

(R)—N-(1,1-dioxo-hexahydro-1λ6-thiopyran-4-ylmethyl)-N-{1-[3-(4-ethoxy-phenyl)-4-oxo-3,4-dihydro-pyrido[2,3-d]pyrimidin-2-yl]-ethyl}-2-(4-fluoro-3-trifluoromethyl-phenyl)-acetamide (8). To a solution of 7 (531 mg, 0.845 mmol) in 8 mL of dichloromethane was slowly added 379 mg (1.69 mmol) of 3-chloroperoxybenzoic acid (77%). The resulting mixture was allowed to stir at room temperature for 3 h. Upon completion, 30 mL of a saturated aqueous sodium thiosulfate solution was added, and the resulting mixture was extracted with dichloromethane (40 mL×3). The combined extracts were washed with a saturated aqueous sodium thiosulfate solution and water, dried over anhydrous sodium sulfate and concentrated in vacuo. The product was purified by column chromatography using 50% and 100% ethyl acetate/hexane successively as the eluents to give 484 mg of 8. $^1$H NMR: a mixture of cis/trans amide rotamers in ca. 4:1 ratio (400 MHz, CDCl$_3$; T=25° C.) δ$_{major}$ 3.60 (d, J=3.60 Hz, 1H), 8.85 (d, J=6.64 Hz, 1H), 7.04-7.68 (m, 8H), 5.13 (q, J=7.29 Hz, 1H), 4.10 (q, J=6.97 Hz, 2H), 3.90 (ABd, J$_{AB}$=16.3 Hz, 1H), 3.59-3.75 (m, 3H), 2.85-3.17 (m, 4H), 1.80-2.35 (m, 5H), 1.46 (J=6.95 Hz, 3H), 1.43 (d, J=7.43 Hz, 3H) and δ$_{minor}$ 9.10 (m, 1H), 8.78 (m, 1H), 1.59 (d, J=6.74 Hz, 3H). MS (ESI$^+$) 661 [M+H]$^+$.

7.7 Example 9

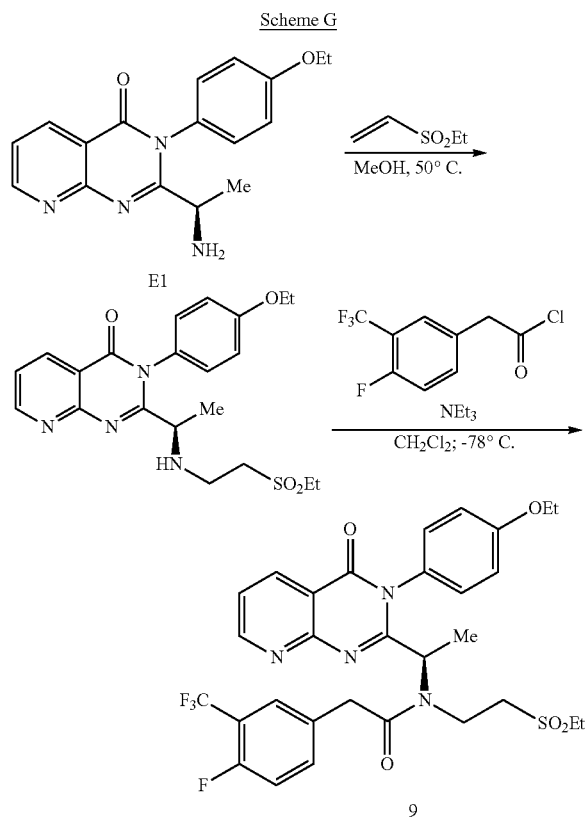

(R)—N-(2-Ethanesulfonyl-ethyl)-N-{1-[3-(4-ethoxy-phenyl)-4-oxo-3,4-dihydro-pyrido[2,3-d]pyrimidin-2-yl]-ethyl}-2-(4-fluoro-3-trifluoromethyl-phenyl)-acetamide (9). Compound 9 was synthesized in two steps from E1 following the synthetic sequence for 2. $^1$H NMR for 9: a mixture of cis/trans amide rotamers in ca. 1.2:1 ratio (400 MHz, CDCl$_3$; T=25° C.) δmajor 8.94 (dd, J=4.60, 2.00 Hz, 1H), 8.58 (dd, J=7.87, 1.99 Hz, 1H), 7.02-7.55 (m, 8H), 5.21 (m, 1H), 3.82-4.19 (m, 5H), 3.48 (m, 3H), 3.09-3.21 (m, 2H), 2.88-2.93 (m, 2H), 1.41-1.47 (m, 9H) and δ$_{minor}$ 9.05 (dd, J=4.60, 2.02 Hz, 1H), 8.63 (dd, J=7.89, 1.98 Hz, 1H), 5.05 (m, 1H), 3.66 (m, 1H), 2.43 (ABd, J$_{AB}$=16.3 Hz, 1H), 1.58 (d, J=6.89 Hz, 3H), 1.22 (t, J=7.45 Hz, 3H). MS (ESI$^+$) 635 [M+H]$^+$.

7.8 Example 10

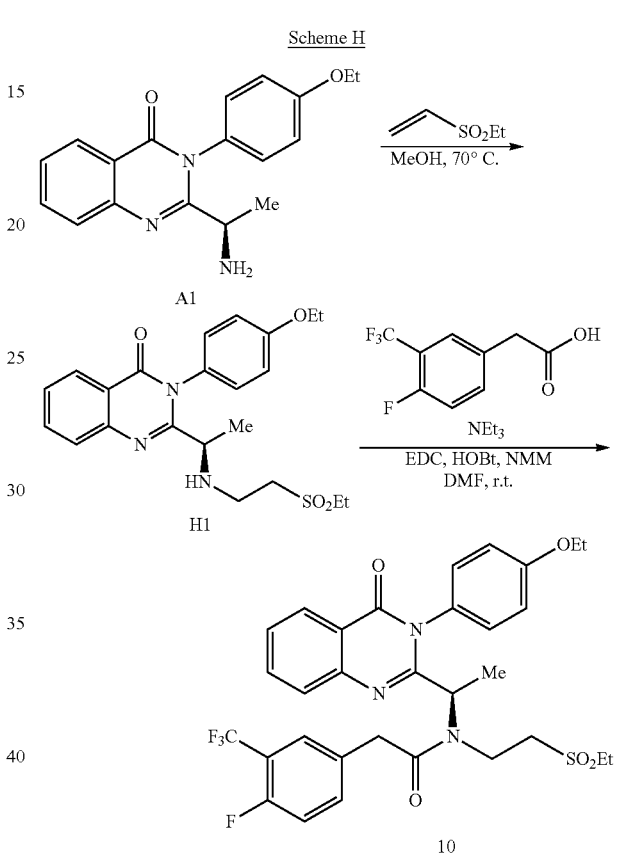

Example 10 was synthesized in two steps from the previously described A1.

(R)-2-[1-(2-Ethanesulfonyl-ethylamino)-ethyl]-3-(4-ethoxy-phenyl)-3H-quinazolin-4-one (H1). A mixture of 0.2 g A1 (0.647 mmol, 1.00 equiv.) and ethyl vinyl sulfone (0.809 mmol, 1.25 equiv.) in 5 mL methanol was stirred at 70° C. for 5 h, then the solution was concentrated in vacuo. The product was used without further purification in the next step. MS (ESI$^+$) 430.1 (MH$^+$).

(R)—N-(2-Ethanesulfonyl-ethyl)-N-{1-[3-(4-ethoxy-phenyl)-4-oxo-3,4-dihydro-quinazolin-2-yl]-ethyl}-2-(4-fluoro-3-trifluoromethyl-phenyl)-acetamide (10). EDC (184 mg, 0.96 mmol) was added to a mixture of compound H1 (137 mg, 0.32 mmol), 4-fluoro-3-trifluoromethylphenylacetic acid (108 mg, 0.49 mmol), HOBt (22 mg, 0.16 mmol) and NMM (97 mg, 0.96 mmol) in 5 mL of DMF. The mixture was stirred at room temperature overnight and then diluted with ethyl acetate. The solution was washed by saturated aqueous sodium bicarbonate, water and brine, dried over anhydrous sodium sulfate, and concentrated. The residue was purified by chromatography to afford a white solid (160 mg). $^1$H NMR (CDCl$_3$) {mixture of cis:trans amide rotamers in ca. 2.57:1 ratio} 1.31 (t, 2.16H, J=7.5 Hz), 1.46 (m, 4.68H), 1.56 (d, 2.16H, J=7 Hz), 2.5 (d, 0.72H, J=16.5 Hz), 2.98 (m, 3H), 3.28 (m, 1H), 3.55 (m, 0.28H), 3.72 (m, 1H), 3.82 (m, 0.56H), 3.95 (m, 0.72H), 4.11 (m, 2.72H), 5.00 (q, 0.72H, J=7 Hz), 5.28 (q, 0.28H, J=7 Hz), 7.05 (m, 0.72H), 7.16 (m, 5.28H), 7.29 (m, 1H), 7.49-7.61 (m, 2H), 7.80 (m, 0.28H), 7.86 (m, 0.72H), 8.31 (d, 1H, J=7.5 Hz). MS (ESI+) 634.1 (MH+).

7.9 Example 11

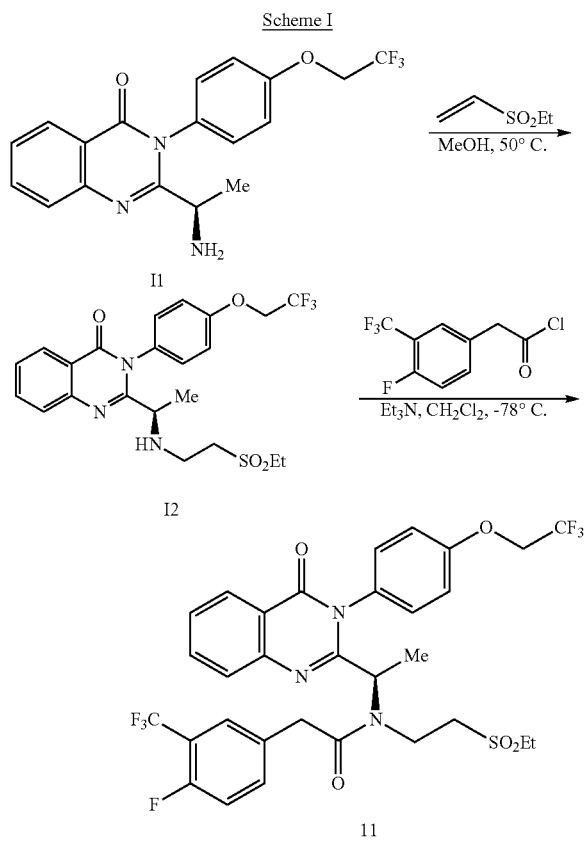

The compound I1 was synthesized as outlined in International Publication No. WO 02/83143, Scheme 3, page 77, except that 4-(2,2,2-trifluoroethoxy)aniline was used in place of p-phenetidine in step b. Compound 11 was synthesized from previously described I1 in two steps as shown in Scheme I.

(R)-2-[1-(2-Ethanesulfonyl-ethylamino)-ethyl]-3-[4-(2,2,2-trifluoroethoxy)-phenyl]-3H-quinazolin-4-one (12). Previously described I1 (158 mg, 0.43 mmol) and ethyl vinyl sulfone (68 μL, 0.65 mmol) were dissolved in methanol and stirred at 60° C. for 3 h. The methanol was removed in vacuo, yielding 210 mg of 12, which was carried forward directly. MS (ESI+): m/z=484.1 [M+H]+.

(R)—N-(2-Ethanesulfonyl-ethyl)-2-(4-fluoro-3-trifluoromethyl-phenyl)-N-(1-{4-oxo-3-[4-(2,2,2-trifluoroethoxy)-phenyl]-3,4-dihydro-quinazolin-2-yl}-ethyl)-acetamide (11). 4-Fluoro-3-trifluoromethylphenylacetic acid (164 mg, 0.74 mmol) was dissolved in dichloromethane and cooled to 0° C. Oxalyl chloride (64 μL, 0.74 mmol) was added, then after 5 min., N,N-dimethylformamide (5.7 μL, 0.07 mmol) was added. The reaction stirred at 0° C. for 30 min. and room temperature for 1 h. The solution was added slowly to a mixture of 12 (210 mg, 0.43 mmol) and triethylamine (182 μL, 1.30 mmol) in dichloromethane at −78° C. This stirred for 30 min., then was washed with saturated aqueous sodium bicarbonate and brine. It was dried over magnesium sulfate, filtered, and concentrated in vacuo. Purified by reverse-phase HPLC to yield 256 mg of a colorless solid, 11. MS (ESI+): m/z=715.2 [M+H]+. $^1$H NMR (500 MHz; CDCl$_3$; T=298 K): δ 9.10-8.95 (m, 1H), 8.66-8.58 (m, 1H), 7.78-7.57 (m, 1H), 7.47-7.36 (m, 3H), 7.24 (m, 1H), 7.13 (m, 3H), 5.03 (q, 1H, J=7.4 Hz), 4.43 (quint, 2H, J=8.0 Hz), 3.77 (s, 1H), 3.71 (m, 1H), 3.62-3.49 (m, 2H), 3.23-3.09 (m, 3H), 2.81 (d, 1H, J=12.9 Hz), 2.62-2.41 (m, 1H), 2.14-1.90 (m, 2H), 1.68 (broad s, 2H), 1.64-1.45 (m, 3H) ppm.

TABLE 2

Examples 12-14

| Example | A⁴ | L | R¹ | R² |
|---------|-----|-----|-----|-----|
| 12 | —N= | —CH$_2$— | —OEt | 3-methyl-1-methyl-pyrazol-5-yl |
| 13 | =CH— | —CH$_2$— | —OEt | CH(Me)CH$_2$-N(cyclobutyl)(Me) |
| 14 | =CH— | absent | —OEt | 4-piperidinyl-N-CH(Me)$_2$ |

7.10 Examples 12-14

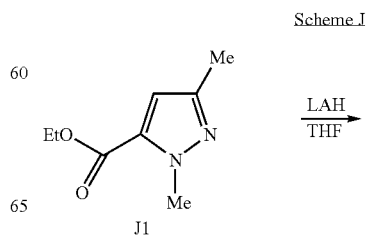

-continued

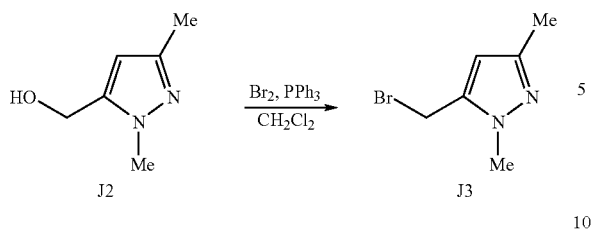

Intermediate J3 was synthesized from commercially available J1 in two steps as shown in Scheme J.

2,5-Dimethyl-2H-pyrazol-3-yl)-methanol (J2). Lithium aluminum hydride (1.0M in tetrahydrofuran, 1.78 mL) solution was added to commercially available ethyl 1,3-dimethyl-1H-pyrazole-5-carboxylate (J1, 300 mg, 1.78 mmol) in tetrahydrofuran over 5 min at room temperature. The reaction stirred overnight. In succession water (67 µL), 15% aqueous sodium hydroxide (202 µL), water (67 µL) were added. The resulting solid was filtered and dried in vacuo, then purified by chromatography (3% to 7% methanol in dichloromethane) to yield 175 mg of a colorless solid, J2.

5-Bromomethyl-1,3-dimethyl-1H-pyrazole (J3). Bromine (229 mg, 1.44 mmol) in dichloromethane was added to a solution of triphenylphosphine (376 mg, 1.44 mmol) in dichloromethane that had been cooled with an ice-water bath. The reaction stirred for 10 min, then J2 (170 mg, 1.34 mmol) was added all at once, whereupon the solution was equilibrated to room temperature over 2 h. The reaction was quenched with water, then the aqueous layer was extracted with dichloromethane (2×25 mL). The combined organic layer was washed with 10% aqueous sodium thiosulfate, then brine. The organic layer was dried over magnesium sulfate, filtered, and concentrated in vacuo. Purified by chromatography (1:1 hexane:ethyl acetate) to yield 195 mg of a colorless solid, J3. $^1$H NMR (400 MHz; CDCl$_3$; T=298 K): δ 6.07 ppm (s, 1H), 4.44 (s, 2H), 3.83 (s, 3H), 2.23 (s, 3H) ppm.

Scheme K

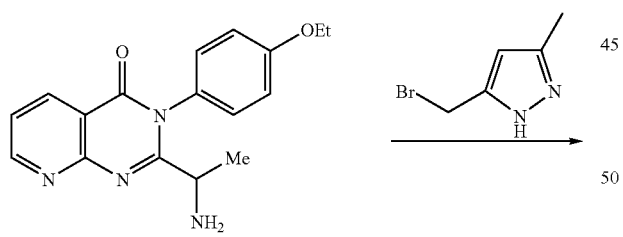

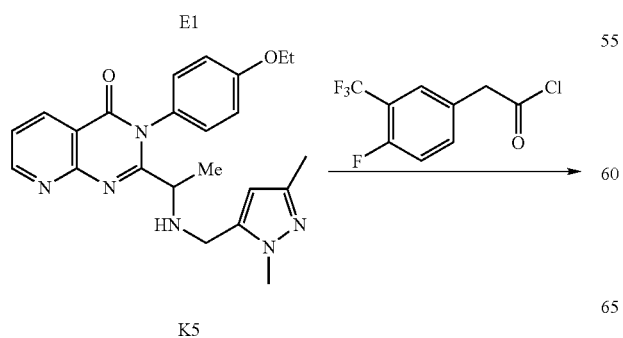

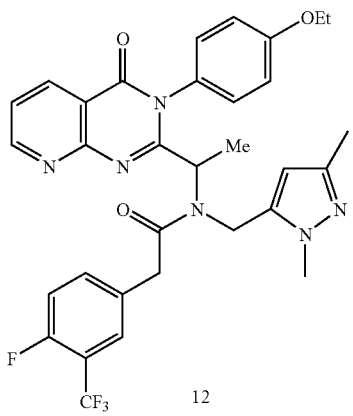

Compound 12 is synthesized from E1 in two steps as shown in Scheme K. E1, J3 and potassium carbonate are reacted in dimethylformamide and the product is purified to yield K5. K5 is reacted with 4-fluoro-3-trifluoromethylphenylacetic acid and oxalyl chloride in triethylamine, dichloromethane and DMF. Compound 14 is filtered and concentrated.

Scheme L

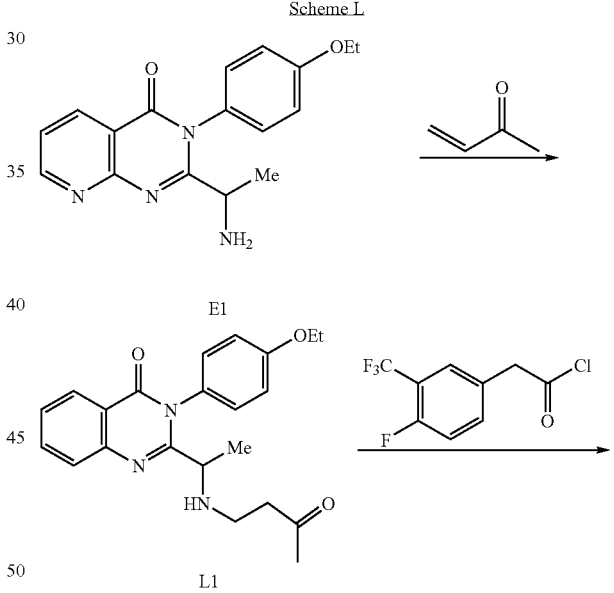

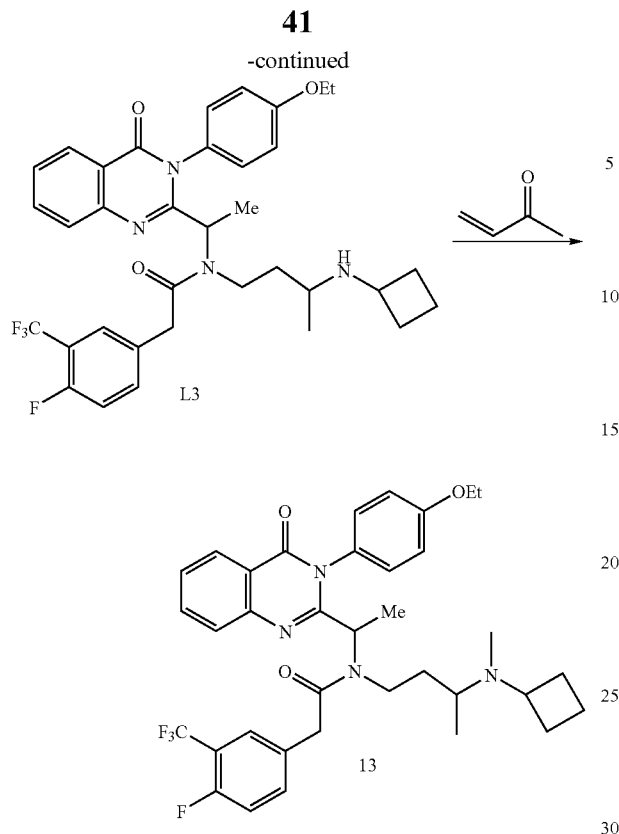

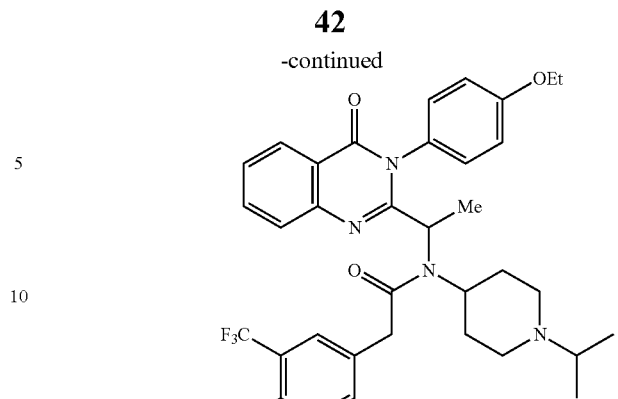

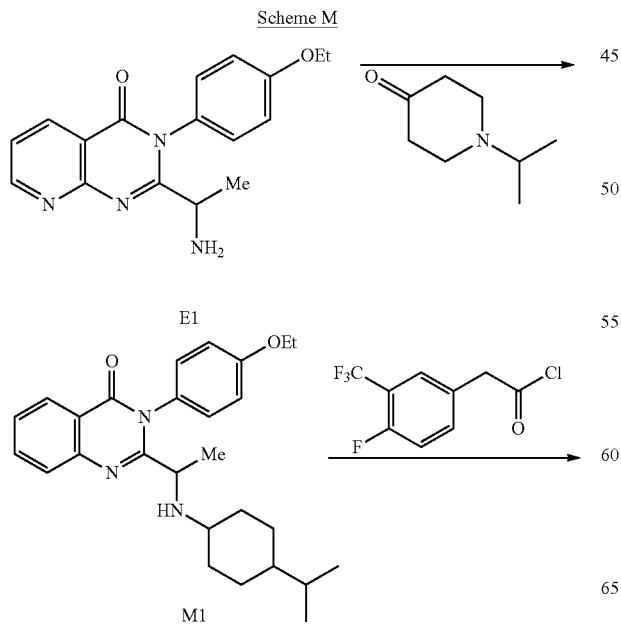

Compound 13 is synthesized from previously described E1 in four steps as shown in Scheme L. E1 and methyl vinyl ketone are reacted and the resulting product is isolated to yield L1. L1 is reacted with 4-fluoro-3-trifluoromethylphenylacetic acid and the resulting product is isolated to yield L2. L2 is reacted with cyclobutyl amine and sodium triacetoxyborohydride and the resulting product is isolated to yield L3. L3 is reacted with formaldehyde and sodium triacetoxyborohydride and the resulting product is isolated to yield 13.

Compound 14 is synthesized from previously described compound E1 as shown in Scheme M. Compound E1, 1-isopropyl-4-piperidone, and sodium triacetoxyborohydride are reacted and the resulting product M1 is isolated. M1, 4-fluoro-3-trifluoromethylphenylacetic acid and oxalyl chloride are reacted and the resulting product is isolated to yield 14.

7.11 Example 15

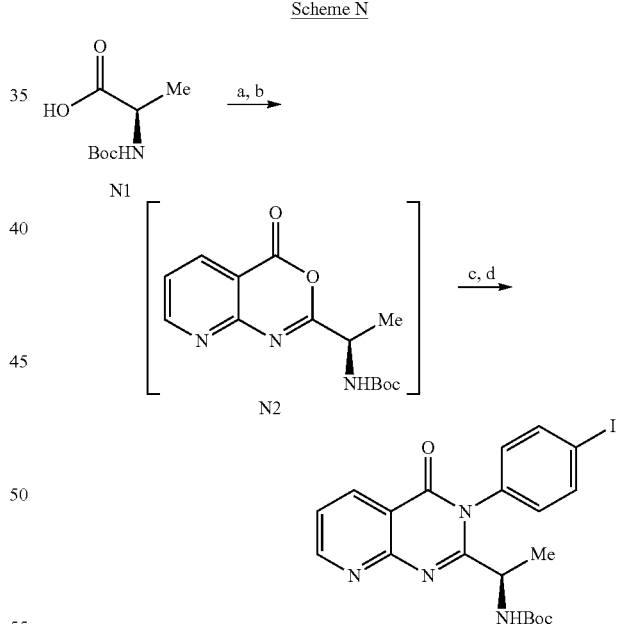

(a) NMM, ICBF, CH$_2$Cl$_2$, -25° C., 1.5 h; (b) 2-aminonicotinic acid, CH$_2$Cl$_2$, -25 to 15° C., 12 h; (c) 1) 4-iodoaniline, CH$_2$Cl$_2$, -10 to 15° C., 12 h; (d) NMM, IBCF, CH$_2$Cl$_2$, -25° C., 12 h (13% overall).

Compound 15 was synthesized from commercially available starting materials as shown in Scheme N.

(R)-tert-butyl 1-(3-(4-iodophenyl)-4-oxo-3,4-dihydropyrido[2,3-d]pyrimidin-2-yl)ethylcarbamate (15). A solution of Boc-d-alanine, N1 (10.0 g, 52.9 mmol) in CH$_2$Cl$_2$ (140 mL) was cooled to −25° C. (measured internally). N-Methylmorpholine (NMM) (13.8 mL, 125 mmol) followed by iso-butylchloroformate (IBCF) (13.5 mL, 104 mmol) were added at such a rate to maintain the internal temperature below −25° C. After 1.5 h the mixture was transferred via cannula to a 250 mL, three-neck flask equipped with a thermometer and containing dry 2-aminonicotinic acid (7.28 g, 52.7 mmol). After the addition was complete (ca. 10 min.) the internal temperature of the mixture was adjusted to −10° C. The reaction mixture was allowed to warm with vigorous stirring over 17 h reaching a final temperature of 15° C. The mixture was cooled to 0° C. and washed with ice-cold 1N HCl (2×100 mL), brine (100 mL) and dried over $Na_2SO_4$. The resulting solution of 2 was charged into a 250 mL three neck, cooled to −25° C. and treated with solid 4-iodoaniline (11.61 g, 53 mmol). The resulting dark mixture was allowed to warm to 15° C. with stirring over 12 h. The solution was washed with 1N HCl (2×100 mL), sat'd $NaHCO_3$ (2×100 mL), brine (100 mL) and dried over $Na_2SO_4$. The mixture was cooled to −25° C. and treated with NMM (6.8 mL, 61.8 mmol) followed by IBCF (6.7 mL, 56.1) maintaining the internal temperature below −25° C. After stirring for 12 h the reaction mixture was washed with 1N HCl (2×100 mL), sat'd $NaHCO_3$ (2×100 mL), brine (100 mL) and dried over $Na_2SO_4$ and concentrated. Purification of the concentrate by silica gel chromatography (50×400 mm column; 5% acetone/$CH_2Cl_2$ to 25% acetone/$CH_2Cl_2$) gave 15 (3.41 g, 13%; purity 96% AUC). $R_f$=0.37 (15% acetone/$CH_2Cl_2$).

7.12 Example 16

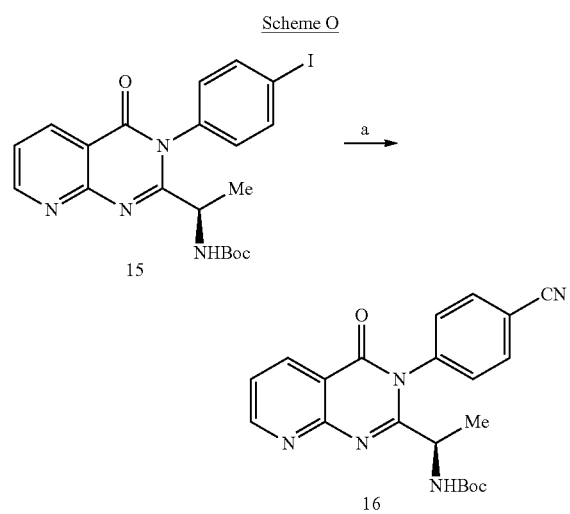

(a) $(Ph_3P)_4Pd$, CuI, NaCN, MeCN, 70° C., 30 min (89%).

(R)-tert-butyl 1-(3-(4-cyanophenyl)-4-oxo-3,4-dihydropyrido[2,3-d]pyrimidin-2-yl)ethylcarbamate (16). Compound 15 (2.02 g, 4.10 mmol), prepared as described in Section 7.11, was combined with $(Ph_3P)_4Pd$ (439 mg, 0.38 mmol), CuI (157 mg, 0.82 mmol) and NaCN (406 mg, 8.29 mmol) in a 25 mL pear shaped flask equipped with a reflux condenser. The mixture was evacuated under high vacuum and backfilled with dry $N_2$ three times. Acetonitrile (6 mL) was then added and the resulting suspension heated to 70° C. for 30 min. at which point TLC and HPLC analysis indicated near complete consumption of 15. The mixture was diluted with EtOAc (100 mL) and filtered through a pad of celite. The filtrate was washed with saturated $NaHCO_3$ (100 mL). The aqueous wash was extracted with additional EtOAc (2×50 mL). The combined extracts were dried over $Na_2SO_4$ and concentrated. Purification of the residue by silica gel chromatography (50×400 mm column; 80% EtOAc/hexanes to 100% EtOAc) gave 16 (1.42 g, 89%; purity 96% AUC; 92% e.e. by chiral HPLC analysis). Rf=0.35 (80% EtOAc/hexanes).

7.13 Example 17

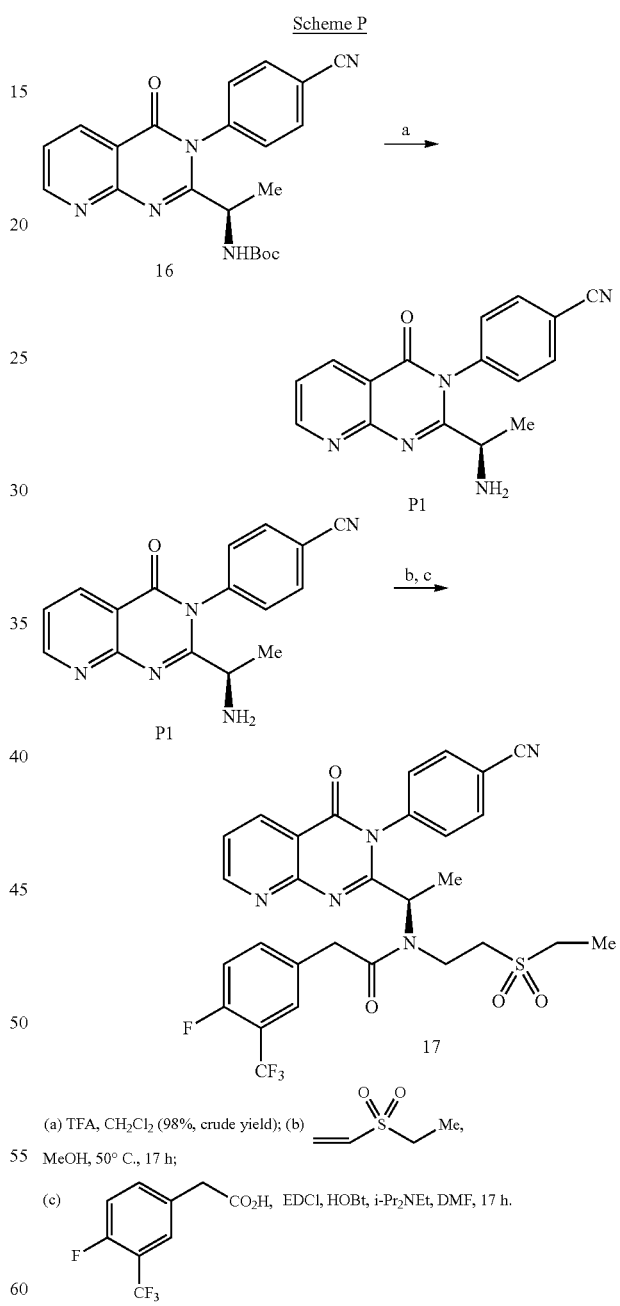

(a) TFA, $CH_2Cl_2$ (98%, crude yield); (b) MeOH, 50° C., 17 h;

(c) [structure] $CO_2H$, EDCl, HOBt, i-$Pr_2NEt$, DMF, 17 h.

(R)-4-(2-(1-aminoethyl)-4-oxopyrido[2,3-d]pyrimidin-3 (4H)-yl)benzonitrile (P1). Compound 16 (1.05 g, 2.68 mmol), prepared as described in Section 7.12, was dissolved in $CH_2Cl_2$ (40 mL) and treated with TFA (40 mL). The resulting mixture was stirred for 1.5 h then concentrated in vacuo.

The concentrate was re-dissolved in CH₂Cl₂ (100 mL) and washed with saturated NaHCO₃ (100 mL). The aqueous wash was extracted with additional CH₂Cl₂ (3×50 mL). The combined extracts were dried over Na₂SO₄, concentrated and dried under high vacuum for 17 h to give P1 (767 mg, 98%), which was suitable for use without further purification.

(R)N-(1-(3-(4-cyanophenyl)-4-oxo-3,4-dihydropyrido[2,3-d]pyrimidin-2-yl)ethyl)-N-(2-(ethylsulfonyl)ethyl)-2-(4-fluoro-3-(trifluoromethyl)phenyl)-acetamide (17). Crude P1 (567 mg, 1.95 mmol) and ethylvinylsulfone (0.26 mL, 2.49 mmol) were combined in anhydrous MeOH (6.5 mL). The mixture was heated to 50° C. (external temperature) with stirring for 17 hours, at which time LC-MS analysis of the reaction mixture indicated complete consumption of the starting material. The reaction mixture was partitioned between EtOAc (100 mL) and water (50 mL). The EtOAc layer was washed with water (2×50 mL). The combined washes were extracted with EtOAc (2×50 mL). The combined extracts were dried over Na₂SO₄ and concentrated. The residue was combined with 4-flouro-3-triflouromethylphenylaceticacid (680 mg, 2.93 mmol), EDCI (2.98 mmol) and HOBt (376 mg, 2.78 mmol) in DMF (5 mL). The resulting mixture was treated with Hunig's base (1.35 mL, 7.75 mmol) and allowed to stir at room temperature for 17 hours. The reaction mixture was diluted with EtOAc (200 mL) and washed with 1N HCl (2×100 mL). The combined washes were extracted with EtOAc (2×100 mL). The combined extracts were washed with saturated NaHCO₃ (200 mL), water (3×100 mL) and brine (100 mL), then dried over Na₂SO₄ and concentrated. The residue was purified by silica gel chromatography (10% THF/CH₂Cl₂ to 20% THF/CH₂Cl₂ to 100% TBF) to give 17 (780 mg, 1.27 mmol, 65%) as an amorphous white solid with >97% purity AUC at 254 nM. R_f=0.2 (15% THF/CH₂Cl₂). DSC showed only endothermal event at 179° C. MS (ESI+) 616.6 (MH⁺).

7.14 Example 18

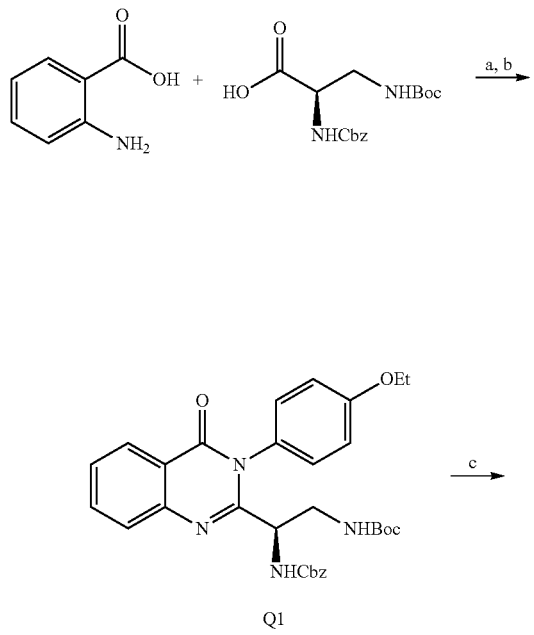

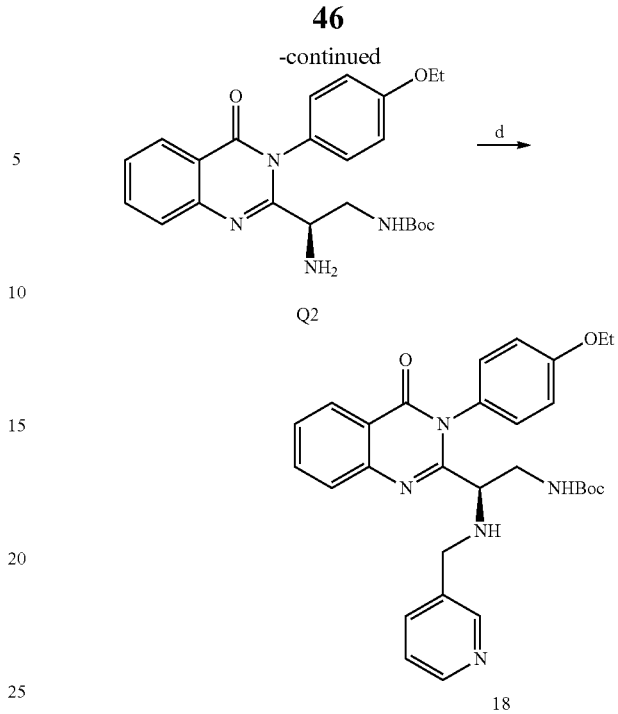

Compound 18 was synthesized from commercially available starting materials in four steps as shown in Scheme Q.

(R)-{2-tert-Butoxycarbonylamino-1-[3-(4-ethoxy-phenyl)-4-oxo-3,4-dihydro-quinazolin-2-yl]-ethyl}-carbamic acid benzyl ester (Q1). To a solution of anthranilic acid (1.86 g, 13.59 mmol) and R-2-benzyloxycarbonylamino-3-tert-butoxycarbonylamino-propionic acid (4.6 g, 13.59 mmol) in 25 mL of anhydrous pyridine was added triphenylphosphite (8.43 g, 27.18 mmol) at room temperature. The resulting solution was stirred at 60° C. for 15 h. p-phenetidine (1.86 g, 13.59 mmol) was added via syringe. The reaction mixture was stirred for another 3 h at 60° C., cooled to room temperature, and evaporated in vacuo to remove most of pyridine. The residue in ether was washed successively with 1N HCl, 1N NaOH, water and brine. The organic layer was dried over anhydrous sodium sulfate and evaporated in vacuo to give a brown residue, which was purified by chromatography to give Q1 as a white solid (4.48 g). MS (ESI⁺) 559.2 (MH⁺).

(R)-{2-Amino-2-[3-(4-ethoxy-phenyl)-4-oxo-3,4-dihydro-quinazolin-2-yl]-ethyl}-carbamic acid tert-butyl ester (Q2). To a solution of Q1 (1 g, 1.79 mmol) and cyclohexa-1,3-diene (2.87 g, 35.84 mmol) in 30 mL of ethanol was added 10% palladium on activated carbon (0.19 g, 0.18 mmol). The resulting solution was refluxed for 3 h. The mixture was filtered and evaporated in vacuo to afford a white solid (0.53 g). ¹H NMR (CDCl₃) 1.35 (s, 9H), 1.48 (t, 3H, J=7 Hz), 3.42 (m, 2H), 3.80 (s, 1H), 4.11 (q, 2H, J=7 Hz), 5.09 (m, 1H), 7.06 (m, 2H), 7.22 (d, 1H, J=8.5 Hz), 7.29 (m, 1H), 7.50 (t, 1H, J=7.5 Hz), 7.72 (m, 1H), 7.79 (m, 1H), 8.30 (d, 1H, J=8.0 Hz) ppm. MS (ESI⁺) 425.2 (MH⁺).

(R)-{2-[3-(4-Ethoxy-phenyl)-4-oxo-3,4-dihydro-quinazolin-2-yl]-2-[(pyridin-3-ylmethyl)-amino]-ethyl}-carbamic acid tert-butyl ester (18). Pyridine-3-carbaldehyde (0.13 g, 1.2 mmol) was added to a solution of compound Q2 (0.424 g, 1 mmol) in dichloroethane (10 mL) at −10° C., followed by sodium triacetoxy borohydride (0.32 g, 1.5 mmol). The mixture was kept at that temperature for 1.5 h, then warmed slowly to room temperature and stirred overnight. The solution was diluted with dichloromethane, washed by saturated aqueous sodium bicarbonate, water, brine and dried over anhydrous sodium sulfate. The solvent was evaporated and yellow solid (0.50 g) compound 18 was obtained. MS (ESI⁺) 516.2 (MH⁺).

TABLE 3

Examples 19-21

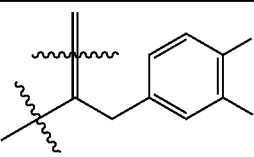

| Example # | X | Y | R |
|---|---|---|---|
| 19 | —N= | 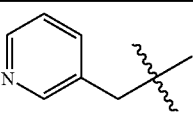 | 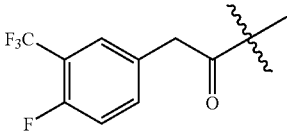 |
| 20 | —NH— | —CH$_2$CH$_2$— | 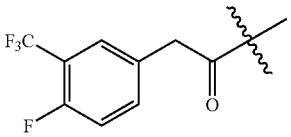 |
| 21 | —NMe— | —CH$_2$CH$_2$— | 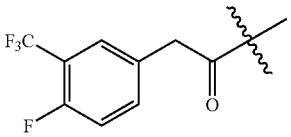 |

7.15 Example 19

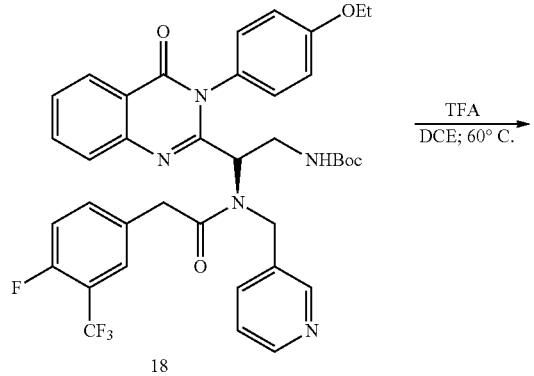

(R)-3-(4-Ethoxy-phenyl)-2-[2-(4-fluoro-3-trifluoromethyl-benzyl)-3-pyridin-3-ylmethyl-4,5-dihydro-3H-imidazol-4-yl]-3H-quinazolin-4-one (19). Trifluoroacetic acid (3.38 g, 3.34 mmol) was added to a solution of compound 15 (0.12 g, 0.167 mmol) in dichloroethane (3 mL). The mixture was heated to 60° C. for 1.5 h. The solvent was removed and the residue was dissolved in ethyl acetate and washed with saturated aqueous sodium bicarbonate, water, brine and dried over anhydrous sodium sulfate. The solvent was removed and the residue was subjected by flash column to give a white solid (67 mg). $^1$H NMR (CDCl$_3$) 1.49 (t, 3H, J=6.96 Hz), 3.89-4.12 (m, 6H), 4.33 (m, 1H), 4.53 (m, 2H), 6.48 (m, 1H), 6.84 (m, 1H), 7.06 (m, 2H), 7.24-7.36 (m, 4H), 7.57 (m, 1H), 7.68 (m, 1H), 7.80-7.90 (m, 2H), 8.33-8.34 (m, 2H), 8.86 (m, 1H). MS (ESI$^+$) 602.2 (MH$^+$).

7.16 Example 20

Scheme T

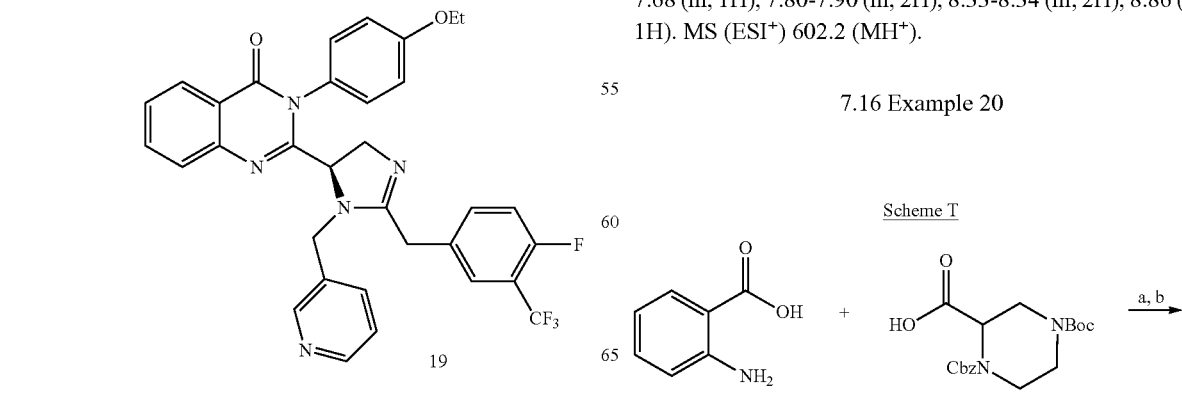

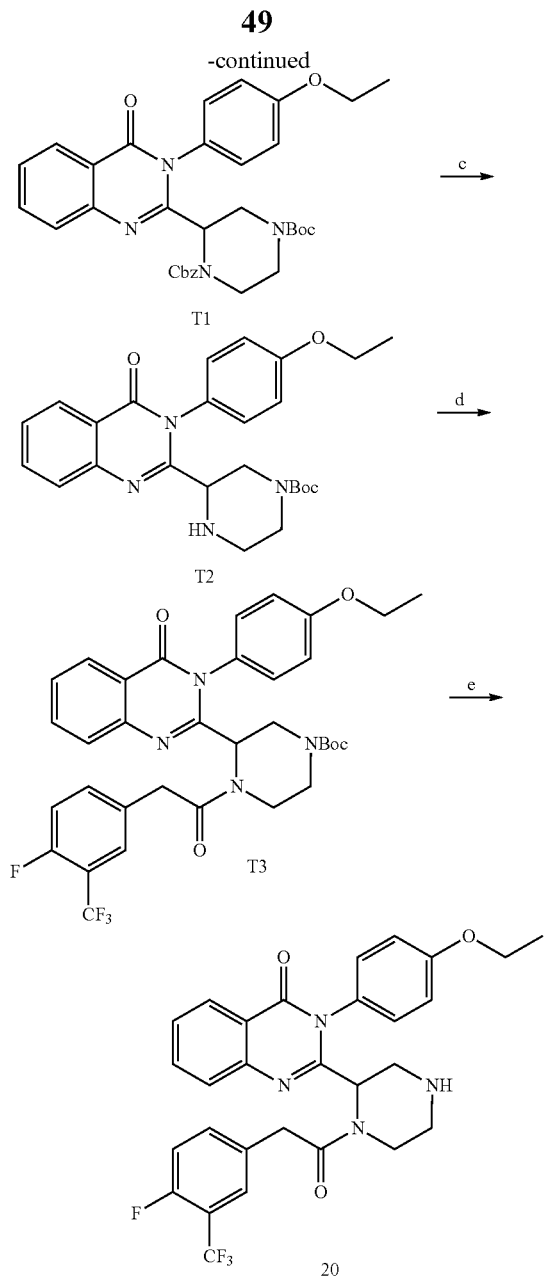

(R)-3-[3-(4-Ethoxy-phenyl)-4-oxo-3,4-dihydro-quinazolin-2-yl]-piperazine-1-carboxylic acid tert-butyl ester (T2). To a solution of compound T1 (2.5 g, 4.28 mmol) and cyclohexa-1,3-diene (6.85 g, 85.62 mmol) in 60 mL of ethanol was added 10% palladium on activated carbon (0.45 g, 0.43 mmol). The resulting solution was refluxed for 3 h. The mixture was filtered and evaporated in vacuo to afford a white solid (1.85 g). $^1$H NMR (CDCl$_3$) 1.43 (s, 9H), 1.49 (t, 3H, J=7 Hz), 2.70 (m, 1H), 2.85 (br, 1H), 2.98 (m, 1H), 3.15 (d, 1H, J=8 Hz), 3.59 (d, 1H, J=8 Hz), 3.95 (br, 1H), 4.13 (m, 3H), 7.08 (m, 2H), 7.24-7.33 (m, 2H), 7.52 (m, 1H), 7.76 (m, 2H), 8.30 (d, 1H, J=7.5 Hz). MS (ESI$^+$) 451.2 (MH$^+$).

(R)-3-[3-(4-Ethoxy-phenyl)-4-oxo-3,4-dihydro-quinazolin-2-yl]-4-[(4-fluoro-3-trifluoromethyl-phenyl)-acetyl]-piperazine-1-carboxylic acid tert-butyl ester (T3). EDC (1.53 g, 8.01 mmol) was added to a mixture of compound T2 (1.2 g, 2.67 mmol), 4-fluoro-3-trifluoromethylphenylacetic acid (0.71 g, 3.20 mmol), HOBt (0.18 g, 1.34 mmol) and NMM (0.81 g, 8.01 mmol) in 15 mL of DMF. The mixture was stirred at room temperature overnight and then diluted with ethyl acetate. The solution was washed by saturated aqueous sodium bicarbonate, water and brine, dried over anhydrous sodium sulfate, and concentrated. The residue was purified by chromatography to afford a white solid (1.44 g). $^1$H NMR (CDCl$_3$) 1.08 (s, 9H), 1.47 (t, 3H, J=7 Hz), 3.05 (m, 2H), 3.67 (m, 1H), 3.81 (m, 2H), 4.10 (m, 3H), 4.24 (m, 1H), 4.49 (m, 1H), 5.19 (m, 1H), 7.11 (m, 3H), 7.29 (m, 1H), 7.51 (m, 5H), 7.75 (m, 1H), 8.30 (d, 1H, J=7.65 Hz) MS (ESI$^+$) 655.2 (MH$^+$).

(R)-3-(4-Ethoxy-phenyl)-2-{1-[(4-fluoro-3-trifluoromethyl-phenyl)-acetyl]-piperazin-2-yl}-3H-quinazolin-4-one (20). Trifluoroacetic acid (5.7 g, 50.15 mmol) was added to a solution of compound T3 (1.64 g, 2.51 mmol) in dichloromethane (90 mL). The mixture was stirred at room temperature for 3 h. The solvent was evaporated, the residue was dissolved in ethyl acetate and washed with saturated aqueous sodium bicarbonate, water, brine and dried over anhydrous sodium sulfate. The solvent was removed and the residue was subjected by flash column to give a white solid (1.28 g). White solid. $^1$H NMR (CDCl$_3$) 1.42 (t, 3H, J=7.04 Hz), 2.69-2.79 (m, 2H), 3.15 (m, 2H), 3.58 (m, 1H), 3.72 (m, 2H), 4.04 (q, 2H, J=7.04 Hz), 4.20 (m, 1H), 5.14 (m, 1H), 6.97-7.15 (m, 4H), 7.34-7.50 (m, 5H), 7.72 (m, 1H), 8.24 (d, 1H, J=7.76 Hz). MS (ESI$^+$) 555.1 (MH$^+$).

Compound 20 was synthesized from commercially available starting materials in five steps as shown in Scheme T.

(R)-2-[3-(4-Ethoxy-phenyl)-4-oxo-3,4-dihydro-quinazolin-2-yl]-piperazine-1,4-dicarboxylic acid 1-benzylester 4-tert-butyl ester (T1). To a solution of anthranilic acid (1.91 g, 13.96 mmol) and piperazine-1,2,4-tricarboxylic acid 1-benzyl ester 4-tert-butyl ester (5.08 g, 13.96 mmol) in 25 mL of anhydrous pyridine was added triphenylphosphite (8.66 g, 27.92 mmol) at room temperature. The resulting solution was stirred at 70° C. for 15 h. pPphenetidine (1.91 g, 13.96 mmol) was added via syringe. The reaction mixture was stirred for another 3 h at 60° C., cooled to room temperature, and evaporated in vacuo to remove most of pyridine. The residue in ether was washed successively with aqueous 1N hydrochloric acid, aqueous 1N sodium hydroxide, water and brine. The organic layer was dried over anhydrous sodium sulfate and evaporated in vacuo to give a brown residue, which was purified by chromatography to give a white solid (2.7 g). MS (ESI$^+$) 585.2 (MH$^+$).

7.17 Example 21

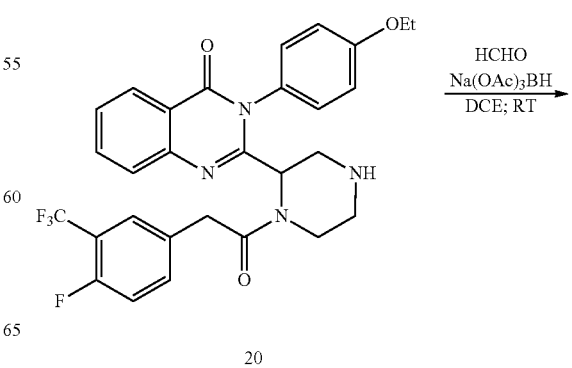

-continued

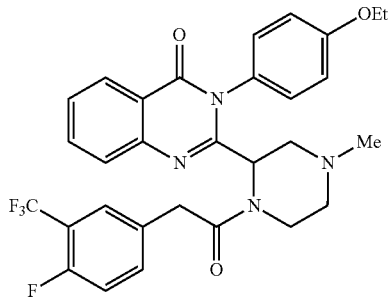

21

(R)-3-(4-Ethoxy-phenyl)-2-{1-[(4-fluoro-3-trifluoromethyl-phenyl)-acetyl]-4-methyl-piperazin-2-yl}-3H-quinazolin-4-one (21). Formaldehyde (37% in water) (0.015 g, 0.18 mmol) was added to a solution of 20 (0.05 g, 0.09 mmol) in dichloroethane (5 mL), followed by Na(OAC)$_3$BH (0.057 g, 0.27 mmol) at room temperature. The mixture was stirred overnight. The solution was diluted with dichloromethane, washed by saturated sodium bicarbonate, water, brine and dried over anhydrous sodium sulfate. The solvent was evaporated and the residue was purified by flash column to afford a white solid (40 mg). $^1$H NMR (CDCl$_3$) 1.42 (t, 3H, J=7.0 Hz), 2.01-2.26 (m, 4H), 2.89 (m, 2H), 3.77 (m, 4H), 4.04 (q, 2H, J=7.0 Hz), 4.46 (m, 1H), 5.41 (m, 1H), 7.01 (m, 3H), 7.06 (m, 1H), 7.41 (m, 5H), 7.71 (m, 1H), 8.21 (d, 1H, J=8.08 Hz). MS (ESI+) 569.2 (MH$^+$).

7.18 Examples 22-52

Examples 22-52 were prepared following the synthesis for examples described above, and in synthetic schemes provided in FIGS. 1, 4, 13, 14 and 16-18 of International Publication WO 02/083143, with slight modifications.

TABLE 1

| Example | Formula | Characterization (Mass, MS + 1) |
|---|---|---|
| 22 | 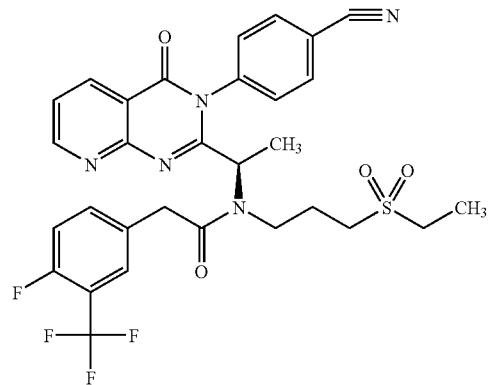 | Chiral 630.6 |
| 23 | 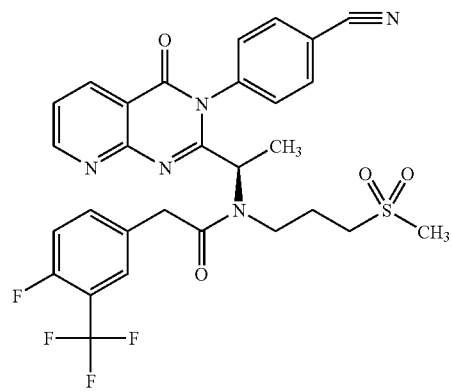 | Chiral 616.6 |

TABLE 1-continued
| Example | Formula | Characterization (Mass, MS + 1) |
|---------|---------|-------------------------------|
| 24 | Chiral 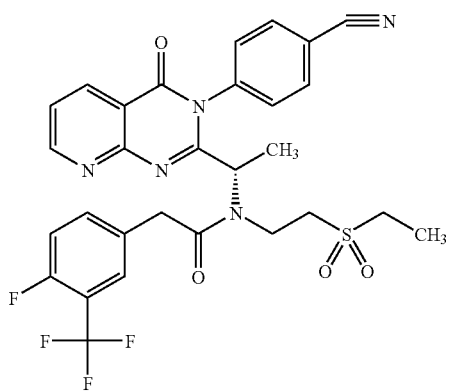 | 616.6 |
| 25 | Chiral 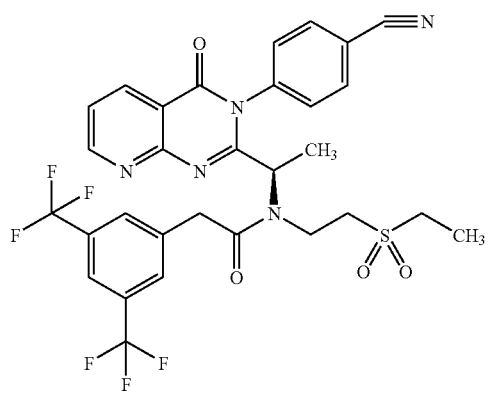 | 666.6 |
| 26 | Chiral 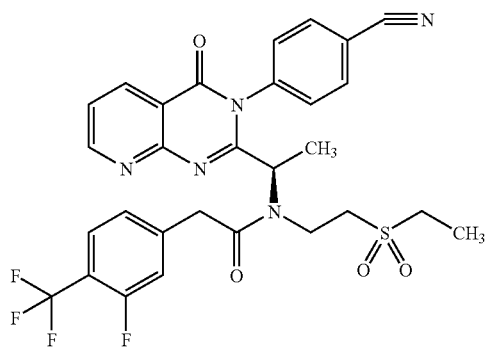 | 616.6 |

TABLE 1-continued
| Example | Formula | Characterization (Mass, MS + 1) | |
|---|---|---|---|
| 27 | | Chiral | 616.6 |
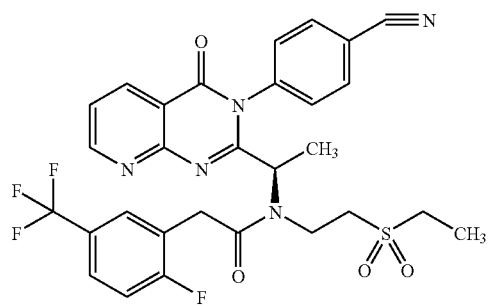
| 28 | | Chiral | 616.6 |
|---|---|---|---|
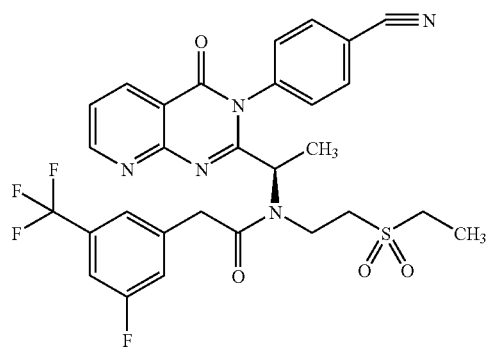
| 29 | | Chiral | 614.6 |
|---|---|---|---|
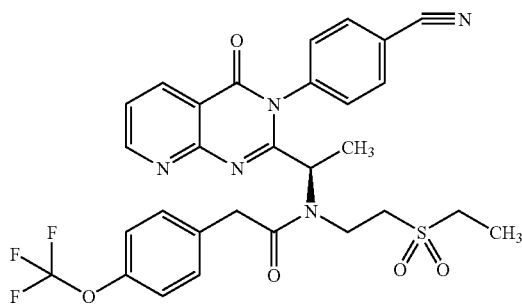
| 30 | | Chiral | 584.6 |
|---|---|---|---|
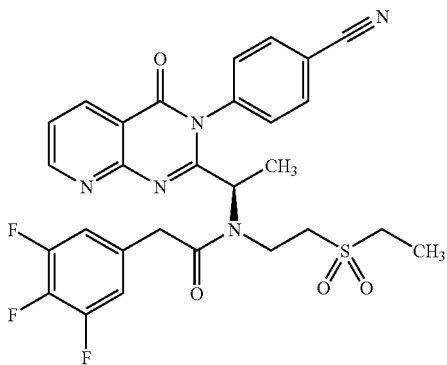

TABLE 1-continued
| Example | Formula | Characterization (Mass, MS + 1) |
|---|---|---|
| 31 | 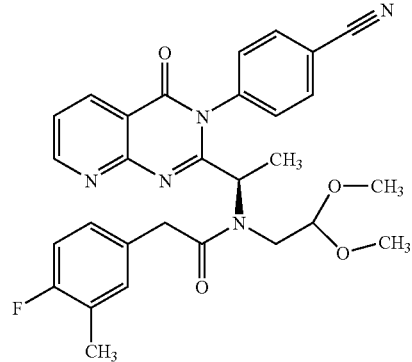 | 584.5 |
| 32 | 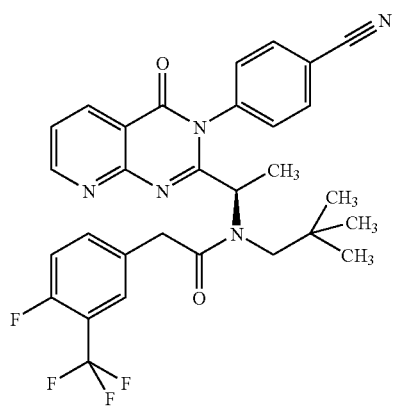 Chiral | 566.6 |
| 33 | 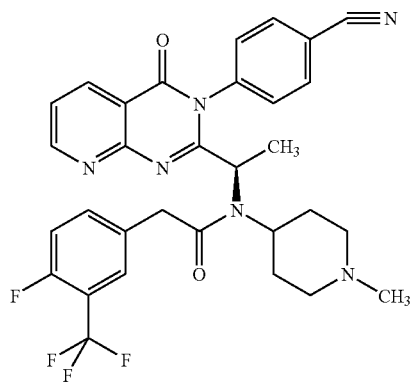 Chiral | 593.6 |

TABLE 1-continued
| Example | Formula | | Characterization (Mass, MS + 1) |
|---|---|---|---|
| 34 | 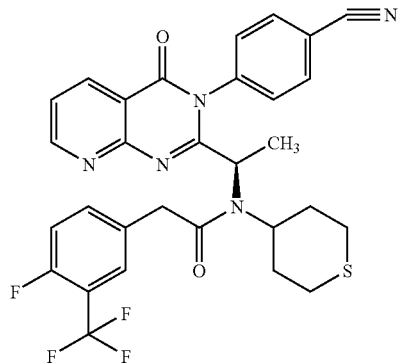 | Chiral | 596.6 |
| 35 | 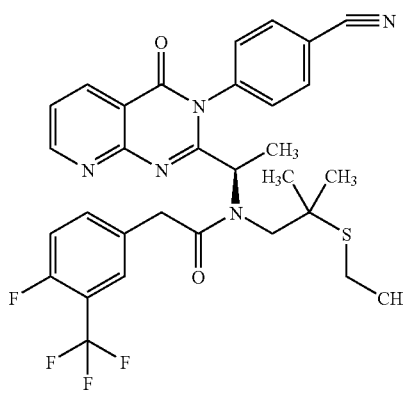 | Chiral | 612.7 |
| 36 | 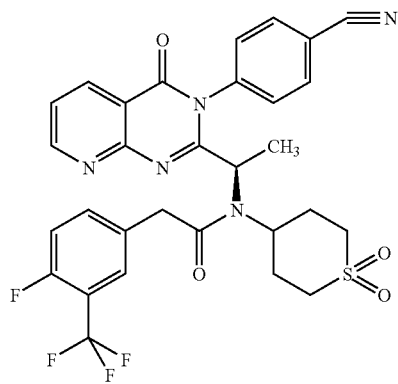 | Chiral | 628.6 |

TABLE 1-continued
| Example | Formula | Characterization (Mass, MS + 1) | |
|---|---|---|---|
| 37 | 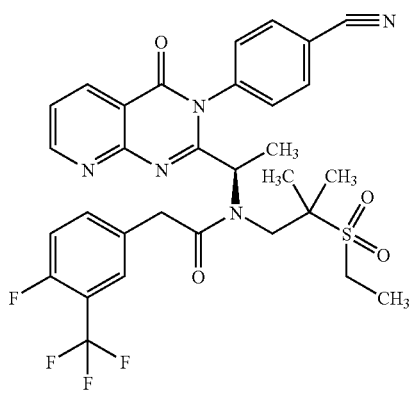 | Chiral | 644.7 |
| 38 | 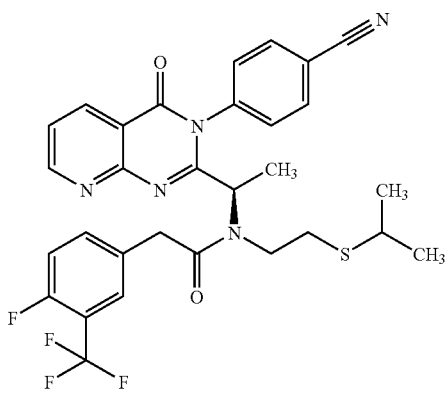 | Chiral | 598.6 |
| 39 | 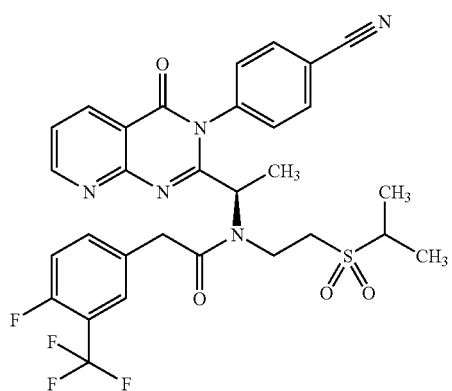 | Chiral | 630.6 |

TABLE 1-continued
| Example | Formula | | Characterization (Mass, MS + 1) |
|---|---|---|---|
| 40 | 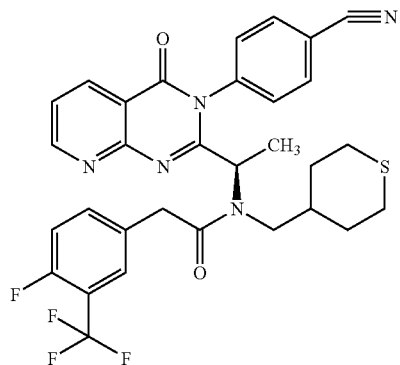 | Chiral | 610.6 |
| 41 | 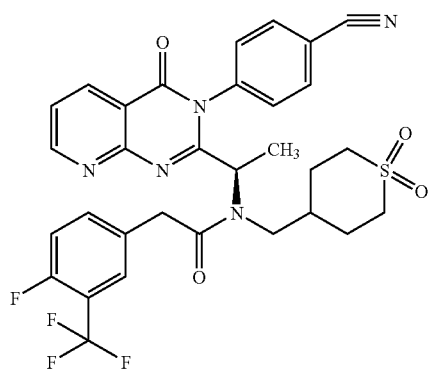 | Chiral | 642.6 |
| 42 | 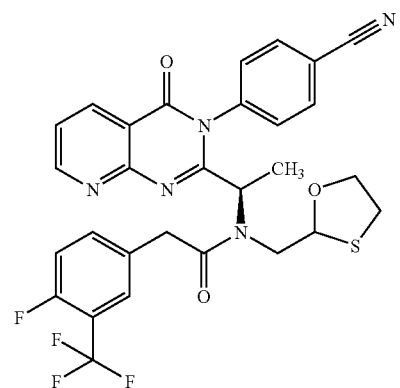 | Chiral | 598.6 |

TABLE 1-continued
| Example | Formula | Characterization (Mass, MS + 1) |
|---|---|---|
| 43 | Chiral 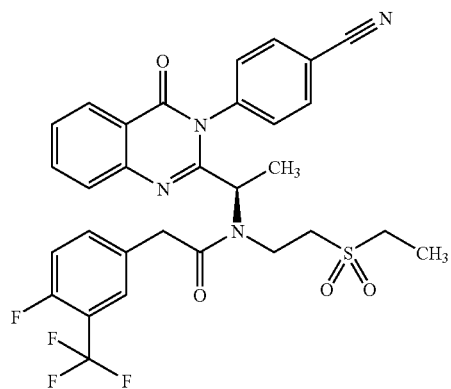 | 615.6 |
| 44 | Chiral 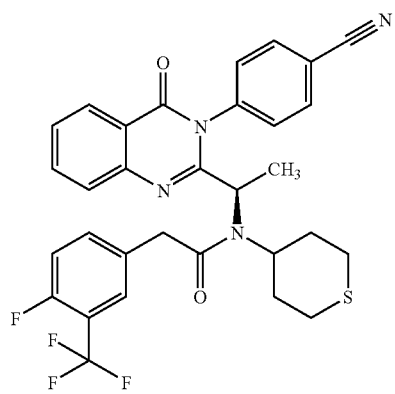 | 595.6 |
| 45 | Chiral 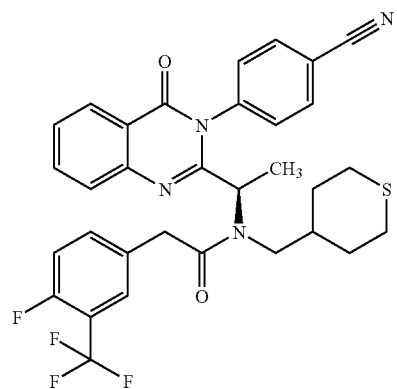 | 609.7 |

TABLE 1-continued
| Example | Formula | Characterization (Mass, MS + 1) | |
|---|---|---|---|
| 46 | | Chiral | 641.7 |
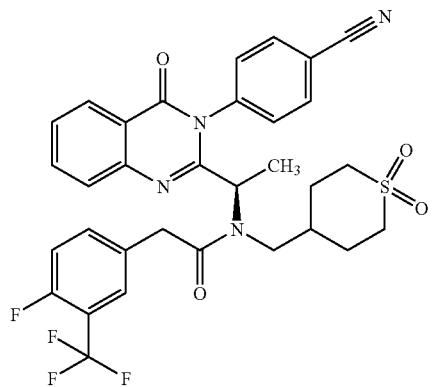
| 47 | | Chiral | 629.6 |
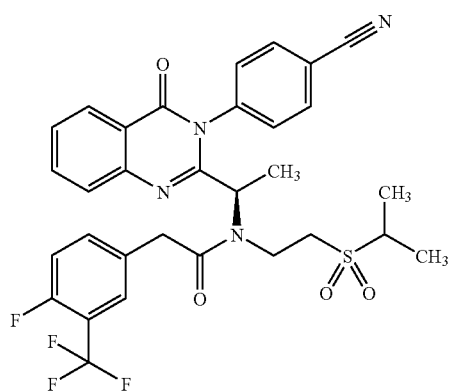
| 48 | | Chiral | 643.7 |
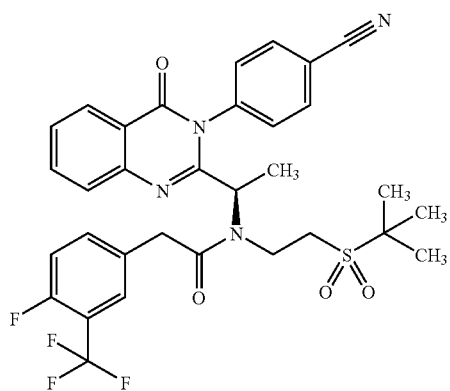

TABLE 1-continued
| Example | Formula | Characterization (Mass, MS + 1) |
|---|---|---|
| 49 | Chiral | 598.6 |
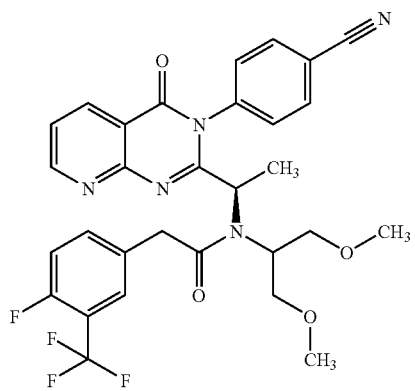
| 50 | Chiral | 644.7 |
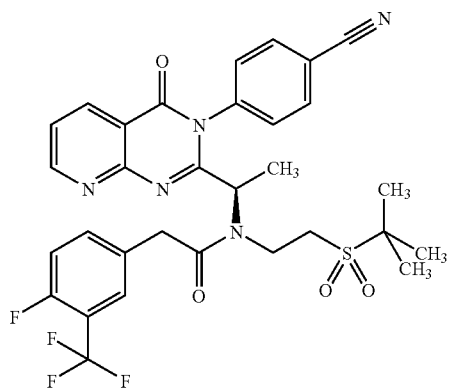
| 51 | Chiral | 615.6 |
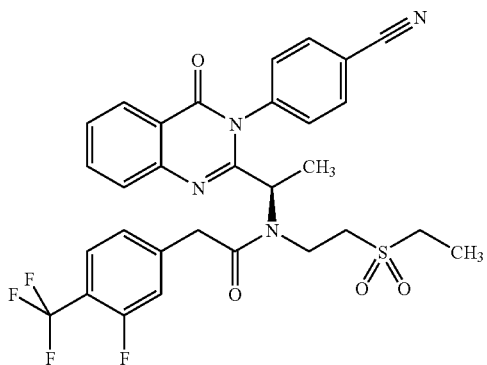

TABLE 1-continued

| Example | Formula | Characterization (Mass, MS + 1) |
|---------|---------|-------------------------------|
| 52 | Chiral | 614.6 |

7.19 CXCR3-Binding and Migration Assays

CXCR3-binding Assay: The following example illustrates a CXCR3 binding assay that can be used for evaluating the compounds of the present invention, as described in Example 12 of International Publication No. WO 02/083143.

Unless otherwise noted, all reagents for the assay are available from commercial sources (e.g., Sigma-Aldrich, St. Louis, Mo., USA). Test compounds are diluted in DMSO to a concentration that is 40-times the intended final assay concentration; 5 μL are transferred to each well of a 96-well flat-bottomed polypropylene plate (e.g., from Greiner, Inc.). Cells expressing CXC3 (see International Publication No. WO 02/083143) are suspended in assay buffer (25 mM Hepes, 80 mM NaCl, 1 mM $CaCl_2$, 5 mM $MgCl_2$, 0.2% bovine serum albumin, pH 7.1, stored at 4° C.) at 5 million cells per mL; 100 μL of this cell suspension is transferred to each well of a 96-well plate containing the diluted test compounds. $^{125}$I-labelled chemokine (purchased from commercial sources, e.g., Amersham, PE Life Sciences) is diluted in assay buffer to a concentration of approximately 60 μM; 100 μL of this chemokine solution is transferred to each well of a 96-well plate containing compounds and cell suspension. The plates can be sealed with commercially available foil plate seals (e.g., from E&K Scientific), and stored at 4° C. for a period of 2 to 4 h, shaking gently. At the end of this incubation period, the contents of the assay plates are transferred to GF/B filter plates (Packard) that have been pre-coated by dipping into a solution containing 0.3% polyethyleneimine (Sigma), using a cell harvester (Packard), and can be washed twice with wash buffer (25 mM Hepes, 500 mM NaCl, 1 mM $CaCl_2$, 5 mM $MgCl_2$, pH 7.1, stored at room temperature). The filter plates are sealed on the bottom with plate seals (Packard), 50 μL of Microscint-20 scintillation fluid (Packard) is added to each well, and the top of the plates are sealed with clear plastic (TopSeal A, Packard). The plates are counted on a scintillation counter, such as a Packard Top-Count. To measure non-specific binding, 4 wells containing unlabelled "cold" chemokine can be included on each 96-well plate. To measure maximum binding, 4 wells containing 5 μL of DMSO, 100 μL of cell suspension and 100 μL of $^{125}$I-labelled chemokine solution can be included on each 96-well plate. Data can be analyzed using commercially available software (e.g., Excel from Microsoft, Prism from GraphPad Software Inc.).

CXCR3 Plasma Migration Assay: The following example provides a CXCR3 plasma migration assay that can be used for evaluating the compounds of the present invention.

Human peripheral blood mononuclear cells (PBMCs) are activated with OKT3 (purified by AB solutions from hybridoma cell line OKT3 (ATCC CRL-8001)) and IL-2 (Peprotech, Inc., Rocky Hill, N.J., USA), and at fourteen days, the cells are loaded with chloromethyl-fluoroscein-diacetate (CMFDA) (Molecular Probes, Inc.) by incubating the activated PBMCs in 1 ng/mL CMFDA for >1.5 hours at 37° C. in a tissue culture incubator. While cells are loading, the test compounds can be diluted in DMSO to a concentration that is 100-times the intended final assay concentration. Next, 100 ng/mL of human ITAC (Peprotech) in human plasma (EDTA, drug free, Biological Specialty Corp) is prepared. Test compounds are added to the human ITAC preparation. Cells are washed once in prewarmed (37° C.) RPMI (Invitrogen) media with 0.5% BSA and resuspended to 5 million cells/ml in human plasma. The test compounds are added to the PBMCs. A 96-well chemotaxis migration plate (NeuroProbe, Inc.) is assembled by adding, per well, 30 uL of ITAC/compound mixture in the lower chamber, placing the impermeable membrane on top of the ITAC/compound well, and adding 50 uL of the PBMC/compound mixture to the well. The plates are covered and can be incubated in a humidified tissue culture incubator for 2.5 hours. A standard curve of CMFDA-loaded cells to be used as a reference for the test plates can be prepared. Migration plates are disassembled and are read in a flourometric plate reader set to 475 nm absorbance, 517 nm emission. The flourometric reading can be converted to cell number using the standard curve and calculating the percentage of migrating cells.

Other assays may be used to identify compounds that modulate CXCR3 chemokine receptor activity, for example, binding assays (see, e.g., Weng et al. (1998) *J. Biol. Chem.* 273:18288-18291, Campbell et al. (1998) *J. Cell Biol.* 141:1053-1059, Endres et al. (1999) *J. Exp. Med.* 189:1993-1998 and Ng et al. (1999) *J. Med. Chem.* 42:4680-4694), calcium flux assays (see, e.g., Wang et al. (2000) *Mol. Pharm.* 57:1190-1198 and Rabin et al. (1999) *J. Immunol.* 162:3840-3850) and chemotaxis assays (see, e.g., Albanesi et al. (2000) *J. Immunol.* 165:1395-1402 and Loetscher et al. (1998) *Eur. J. Immunol.* 28:3696-3705), and other assays known to those of skill in the art.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula (I):

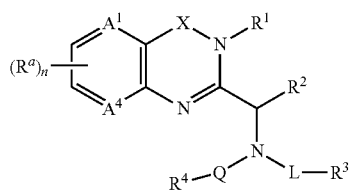

or a pharmaceutically acceptable salt or prodrug thereof, wherein $A^1$ is $C(R^b)$;

$A^4$ or N;

Q is a member selected from the group consisting of a bond, $(C_1-C_8)$alkylene, $(C_2-C_8)$heteroalkylene, —C(O)—, —OC(O)—, —$CH_2CO$—, —$CH_2SO$— and —$CH_2SO_2$—;

L is a bond or $(C_1-C_5)$alkylene;

X is —$CH_2$—, or —C(O)—;

$R^a$ is selected from the group consisting of hydrogen, —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$;

$R^b$ is selected from the group consisting of hydrogen, —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —R', —S(O)R', —S(O)$_2$R', —S(O)$_2$NR'R", —CN and —NO$_2$;

the subscript n is 0, 1 or 2:

each R', R" and R'" independently is H, unsubstituted $(C_1-C_8)$alkyl, heteroalkyl, unsubstituted aryl, or substituted aryl;

$R^1$ is heteroaryl or aryl;

$R^2$ is a member selected from the group consisting of hydrogen, halogen, $(C_1-C_{10})$alkyl, $(C_2-C_{10})$heteroalkyl, hetero$(C_1-C_{10})$cycloalkyl, $(C_1-C_{10})$alkylaryl, and $(C_2-C_{10})$heteroalkylaryl;

$R^3$ is a member selected from the group consisting of —S(O)$_m$R$^5$, —S(O)$_m$N(R$^8$)R$^9$, —S(O)$_m$N(R$^8$)CH$_2$R$^6$, —N(R$^8$)SO$_2$R$^5$,

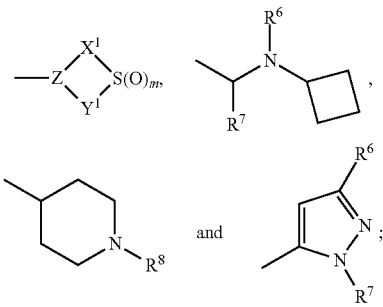

$R^4$ is a member selected from the group consisting of $(C_1-C_{20})$alkyl, $(C_2-C_{20})$heteroalkyl, heteroaryl, aryl, heteroaryl$(C_1-C_6)$alkyl, heteroaryl$(C_2-C_6)$heteroalkyl, aryl$(C_1-C_6)$alkyl and aryl$(C_2-C_6)$heteroalkyl;

$R^5$ is selected from the group consisting of $(C_1-C_8)$alkyl, $(C_2-C_8)$heteroalkyl, aryl and heteroaryl;

$R^6$ and $R^7$ independently are hydrogen, $(C_1-C_8)$alkyl or $(C_2-C_8)$heteroalkyl;

$R^8$ is hydrogen, $(C_1-C_8)$alkyl, $(C_2-C_8)$heteroalkyl, heteroaryl or aryl;

$R^9$ is $(C_1-C_8)$alkyl;

Z is CH or N;

$X^1$ is a bond, $(C_1-C_6)$alkylene or $(C_1-C_6)$heteroalkylene;

$Y^1$ is $(C_1-C_6)$alkylene; and the subscript m is 0, 1 or 2.

2. The compound according to claim 1, wherein $R^3$ is a member selected from the group consisting of —SO$_2$CH$_3$, —SO$_2$CH$_2$CH$_3$,

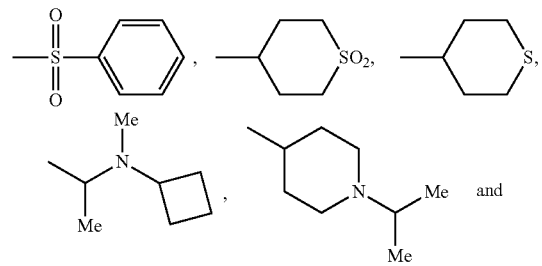

-continued

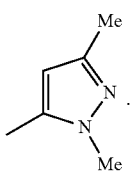

3. The compound according to claim 1, having the formula (Ia):

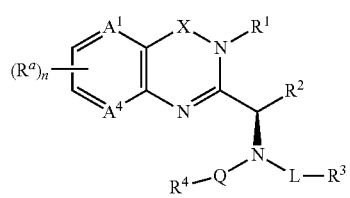

or a pharmaceutically acceptable salt or prodrug thereof.

4. The compound of claim 3, wherein X is —C(O)—.

5. The compound of claim 3, wherein $R^1$ is a unsubstituted or a meta- or para-substituted phenyl, wherein the substituent is a halogen, $(C_1-C_8)$alkyl, $(C_1-C_8)$heteroalkyl, $(C_1-C_8)$alkoxy, or $(C_1-C_8)$heteroalkoxy.

6. The compound of claim 3, wherein $R^2$ is a member selected from the group consisting of

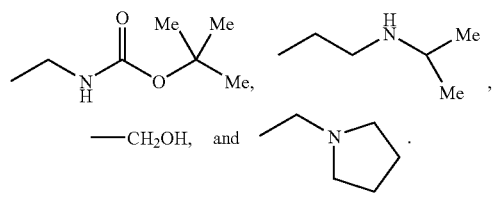

7. The compound of claim 3, wherein Q is —C(O)—.

8. The compound of claim 3, wherein L is a bond, —CH$_2$— or —CH$_2$CH$_2$—.

9. The compound according to claim 3, wherein -L-$R^3$ when taken together is

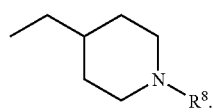

10. The compound of claim 3, wherein -Q-$R^4$ is

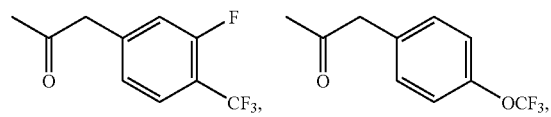

-continued

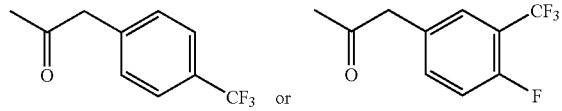

11. The compound of claim 3, wherein $R^1$ is para-cyanophenyl.

12. The compound of claim 3 having the formula (II):

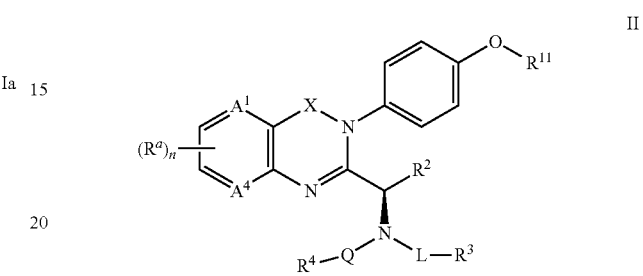

or a pharmaceutically acceptable salt or prodrug thereof, wherein
$R^{11}$ is hydrogen, $(C_1-C_8)$alkyl or $(C_2-C_8)$heteroalkyl.

13. The compound of claim 12, wherein $R^{11}$ is —H, —CH$_3$, —CH$_2$CH$_3$, or —CH$_2$CF$_3$.

14. The compound of claim 12, wherein X is —C(O)—.

15. The compound of claim 12, wherein $R^2$ is methyl and -L-$R^3$ is

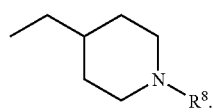

16. The compound of claim 12, wherein $R^3$ is a member selected from the group consisting of —SO$_2$CH$_3$, —SO$_2$CH$_2$CH$_3$,

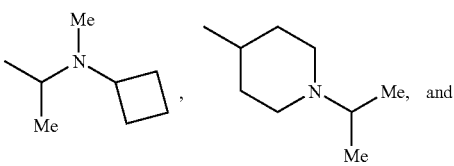

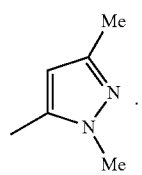

17. The compound of claim 12, wherein -Q-R⁴ is

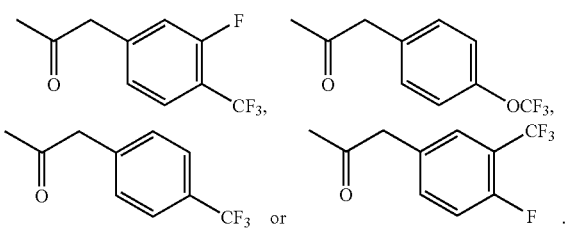

18. The compound of claim 17, wherein R³ is a member selected from the group consisting of —SO₂CH₃, —SO₂CH₂CH₃,

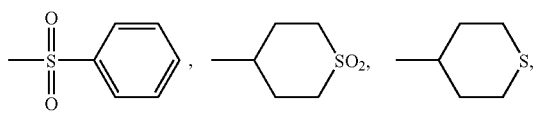

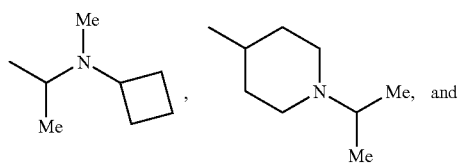

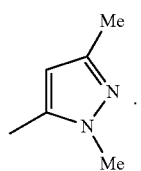

19. The compound of claim 1, wherein the compound is selected from the group consisting of

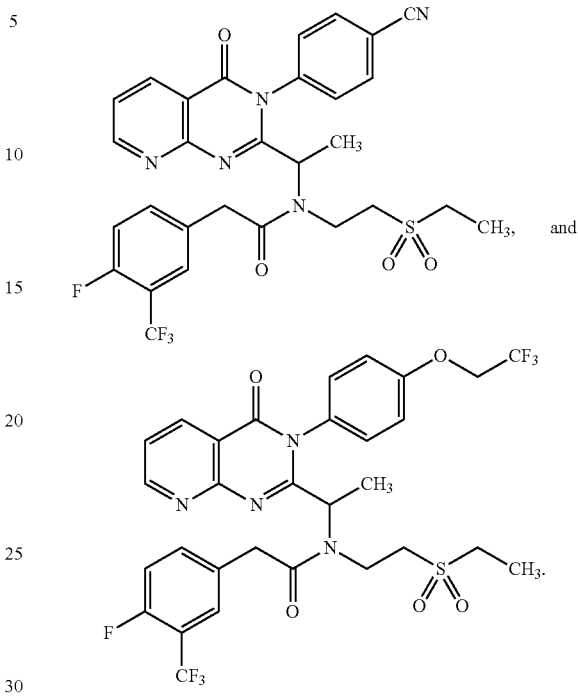

20. A pharmaceutical composition comprising the compound of claim 1 and a pharmaceutically acceptable carrier, diluent or excipient.

21. A pharmaceutical composition comprising the compound of claim 2 and a pharmaceutically acceptable carrier, diluent or excipient.

22. A pharmaceutical composition comprising the compound of claim 3 and a pharmaceutically acceptable carrier, diluent or excipient.

23. A pharmaceutical composition comprising the compound of claim 19 and a pharmaceutically acceptable carrier, diluent or excipient.

* * * * *